United States Patent [19]
Ikeda et al.

[11] Patent Number: 5,334,837
[45] Date of Patent: Aug. 2, 1994

[54] MICRO ANALYTICAL METHOD, SAMPLING PLATE USED IN SAME, METHOD OF DETECTING ORGANIC COMPOUND BY USE OF SAID MICRO ANALYTICAL METHOD, APPARATUS FOR SAME AND METHOD OF DIVIDING FOR MICRO-LIQUID FLOW

[75] Inventors: Masahiko Ikeda, Kusatsu; Hirosi Uchihara, Yamashina, both of Japan

[73] Assignee: Horiba, Ltd., Kyoto, Japan

[21] Appl. No.: 954,267

[22] Filed: Sep. 30, 1992

[30] Foreign Application Priority Data

| Oct. 5, 1991 | [JP] | Japan | 3-285566 |
| Feb. 29, 1992 | [JP] | Japan | 4-079237 |
| May 9, 1992 | [JP] | Japan | 4-143235 |
| Jun. 20, 1992 | [JP] | Japan | 4-186320 |

[51] Int. Cl.$^5$ .................. G01N 21/01; G01N 21/35
[52] U.S. Cl. .................................................. 250/339
[58] Field of Search .................... 436/809; 250/339

[56] References Cited

U.S. PATENT DOCUMENTS 4,823,009  4/1989  Biemann et al. .............. 250/341

FOREIGN PATENT DOCUMENTS

| 250773 | 10/1987 | German Democratic Rep. | 356/246 |
| 61-79142 | 4/1986 | Japan | 250/339 |
| 63-3244 | 1/1988 | Japan | 250/339 |
| 63-96558 | 4/1988 | Japan | 436/809 |
| 2-28533 | 1/1990 | Japan . | |

*Primary Examiner*—Constantine Hannaher
*Attorney, Agent, or Firm*—Poms, Smith, Lande & Rose

[57] ABSTRACT

Microanalytical methods and associated apparatus for detecting and quantifying organic compounds with very high sensitivity utilize reflected or refracted infrared radiation. By depositing microliter sized quantities of the sample containing solution in a drop-by-drop manner on a water-repellent thin film and rapidly evaporating a solvent, a coherently condensed concentric sample is produced having enhanced sample thickness. This sample is irradiated with infrared radiation which is either reflected or transmitted by the material underlying the thin film. Measuring the spectrum of the infrared radiation passing through the sample detects the existence and concentration of the organic compound. The water-repellent thin film may be provided with multiple small scale depressions, pinholes or zones of reduced surface tension for condensing the sample.

28 Claims, 26 Drawing Sheets

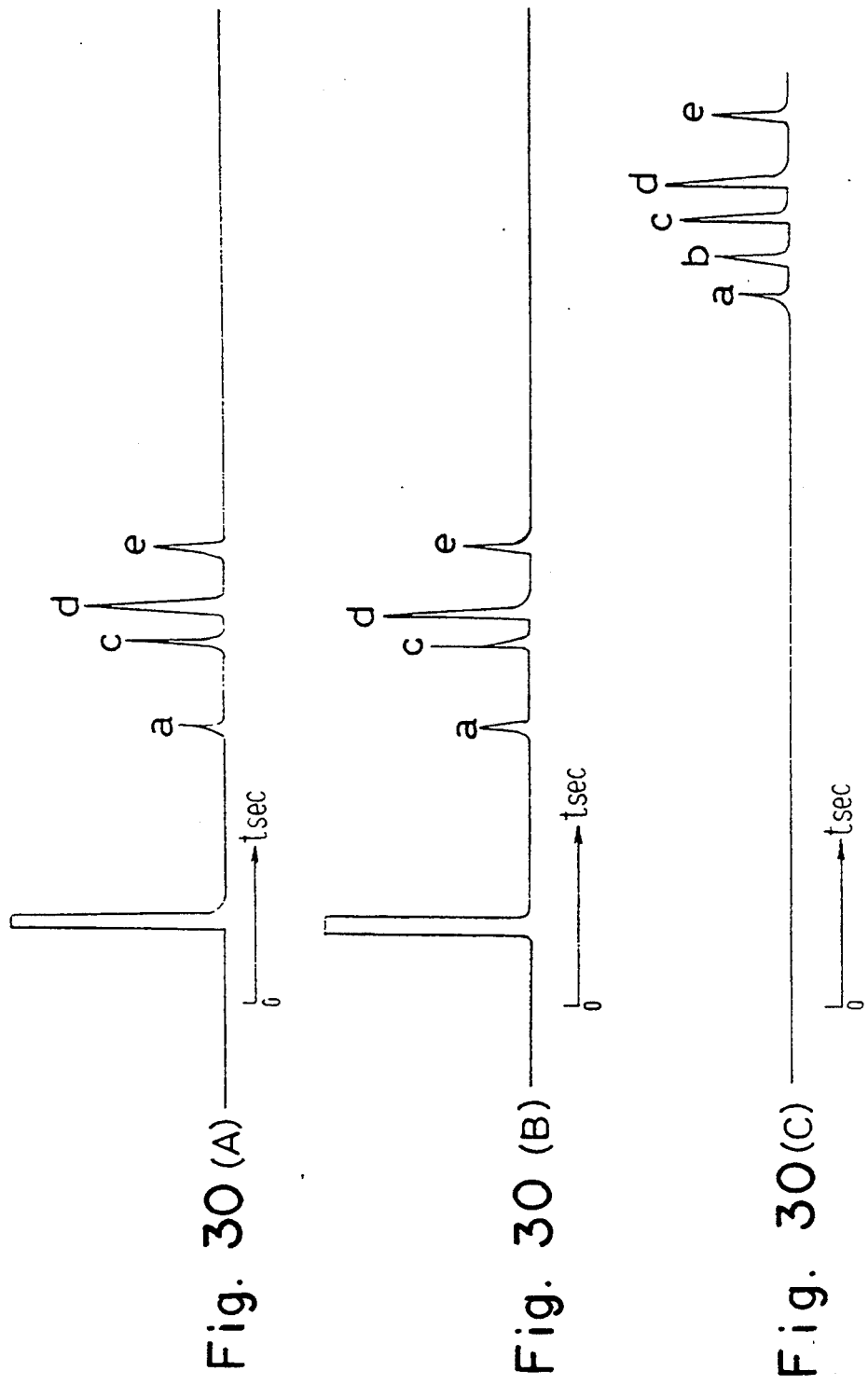

MICRO ANALYTICAL METHOD, SAMPLING PLATE USED IN SAME, METHOD OF DETECTING ORGANIC COMPOUND BY USE OF SAID MICRO ANALYTICAL METHOD, APPARATUS FOR SAME AND METHOD OF DIVIDING FOR MICRO-LIQUID FLOW

BACKGROUND OF THE INVENTION

1. Field of the Invention

The present invention relates to a micro analytical method, a sampling plate used in the same, a method of detecting organic compounds by the use of the micro analytical method, and an apparatus for the same.

2. Description of the Prior Art

Micro analytical methods using, for example, a microscopic FTIR (Fourier Transform Infrared Ray Spectrophotometer), a FTIR with a beam condenser, a FTIR with a condensing lens and the like have been suitable for an analysis of a very small quantity of minute organic matter, but a disadvantage has occurred in the conventional means for condensing a very small quantity of sample in that a condensed sample is diffused to reduce the thickness thereof, thereby reducing the sensitivity.

That is to say, a very small quantity of solution of a solute in a solvent has been deposited drop by drop on a mirror-finished metallic base by the use of an instrument, such as a riffle sampler, and the solvent in the solution has been evaporated to condense the solute on the base, which condensed solution has been used as the sample.

However, by this condensing means, the solution deposited drop by drop on the base has been expanded all over said mirror-finished surface of the base and diffused in the form of islands to be condensed, so that the thickness of said sample has been apt to be reduced.

More concretely speaking, in the case where 1 $\mu l$ of a solution of 10 $\mu l$ of fluid paraffin in 100 ml of acetone has been deposited drop by drop on the base, the solution has been immediately expanded to a circle having a diameter of 3 to 5 mm. The solvent begins to evaporate from a circumferential portion of said circle and at the same time the solute is turned into numerous islands. These islands of solute are condensed in the form of a ring having a diameter of 3 to 5 mm, whereby the thickness of the sample is remarkably reduced.

In this case, the absorption of infrared rays was insufficient. Concretely speaking, a transmission factor of infrared rays measured by a microscopic FTIR/FT-530 (made by HORIBA, Ltd.) was about 98% at a wave number of about 1,450 $cm^{-1}$ as shown in FIG. 38. That is to say, the absorbing degree of light is remarkably low to an extent of 0.01 and thus a highly accurate analysis by the microscopic spectrometric analytical method was difficult.

In addition, the above-described expansion of the solution has no orientation, so that it has been difficult to fix positions where the solute is to be condensed in an appointed manner. This has led to difficulty in the automation of the spectrometric analysis.

Furthermore, disadvantages have occurred in that if positions, where the solution is deposited drop by drop, are allowed to approach so that the solution may be deposited drop by drop at many points compared with the size of a sample table, the solutions deposited drop by drop are brought into contact with each other according to the expansion thereof or the solution deposited drop by drop is attracted to the already condensed sample so as to be brought into contact with it.

By the way, after FTIR has been widely used recently, the so-called HPLC/FTIR, in which a solvent in a solution eluted from HPLC (high-speed liquid chromatography) is removed to be used as a sample in FTIR, has been proposed to be practically used.

Methods of measuring as the above described HPLC/FTIR include for example (1) A method in which an eluted solution is heated, concentrated and removed in sequential phase mode and then a solute is measured by the diffusion-reflection method or the transmission method;

(2) A method in which water is replaced by acetone and methanol by the use of 2,2-dimethoxypropane and acids in an inverted phase mode and acetone and methanol are heated to evaporatively remove solvents and then a solute is measured by the diffusion-reflection method or the transmission method;

(3) A method in which a solute is extracted by the use of chloroform or dichloromethane having a comparatively narrow absorption band in a sequential phase mode to measure a spectrum thereof by the transmission method in the form of liquid or a solvent is evaporatively removed and then a spectrum of a solute is measured by the diffusion-reflection method or the transmission method; and the like.

In any of the above described methods, the sample is irradiated with infrared rays and an absorption spectrum resulting from a vibration causing a change in a dipole moment of molecular vibrations is measured. In these methods, an infrared absorption is characterized in having absorption wavelength bands peculiar to organic functional groups and thus can be applied for qualitatively or quantitatively determining organic functional groups, discriminating similar compounds, making reaction mechanisms clear and analyzing structures, and additionally can analyze a multi-component system comprising at least several kinds of components. However, disadvantages have occurred in that not only is the sensitivity several hundred ng ($10^{-9}$ g) and thus it is unsuitable for a measurement of a very small quantity of component, but also HPLC and the exclusive FTIR are required and thus an apparatus is large-scaled and expensive.

In the case where the FTIR is provided with the above-described HPLC, as shown in FIG. 39, a passage 87 connected with a detector 85 of a liquid chromatograph 86 comprising an eluted liquid tank 81, a liquid-sending pump 82, a sample-injecting portion 83, a partition column 84, detector 85 and the like is provided with a branching T-type joint 88 at an end thereof, tubes 89, 90 having suitable inside diameters being connected with joint 88, and one tube 89 being connected with an analyzer 91 while the other tube 90 is connected with an exhaust passage (not shown). In addition, reference numeral 92 designates a syringe for injecting the sample and reference numeral 93 designates a recorder.

In order to set a flow rate of a liquid flowing through each tube 89, 90, respectively, for example the following measures have been used:

① The inside diameters of the tubes 89, 90 are changed;

② Lengths of the tubes 89, 90 are changed; and

③ The tube 89 connected with analyzer 91 is provided with flow rate-setting means such as a needle valve.

However, according to the above described ①, the ratio of the flow rate of the liquid flowing through tube 89 to that of the liquid flowing through tube 90 is equal to the ratio of the square of the diameters but cannot be continuously changed.

According to ②, a continuous ratio can be obtained but not a length from detector 85 of liquid chromatograph 86 to analyzer 91 is changed and thus the time required for the movement of liquid is varied, but also long tubes are required in order to obtain an increased ratio.

In addition, according to ③, although not only a continuous ratio can be obtained but also the time required for the movement of liquid is not varied. For example, in case of an eluted liquid, a problem has arisen in that the current of the eluted liquid is made turbulent by the needle valve to expand a chromatogram, whereby it becomes difficult to maintain resolution power.

SUMMARY OF THE INVENTION

The present invention has been achieved paying attention to the above described matters. It is a first object of the present invention to develop means for coherently condensing a solution, to provide a micro spectrometric analytical method capable of analyzing a sample in high sensitivity even though a very small quantity of minute solution is used as the sample, and to provide a sampling plate used in the method.

It is a second object of the present invention to provide a method of detecting organic compounds capable of analyzing also a very small quantity of component in high sensitivity by the use of the micro analytical method and an inexpensive apparatus simple in construction for detecting organic compounds.

In addition, it is a third object of the present invention to provide a method of making a liquid branch capable of dividedly sampling a micro-liquid flow, such as eluted liquid in a liquid chromatograph, at an optional ratio.

That is to say, one of the basic micro spectrometric analytical methods according to the present invention is characterized in that a very small quantity of solution of a solute in a solvent is deposited drop by drop on a thin film made of water-repellent resins, such as fluoride family resins, mounted on an infrared ray-reflecting member of a sample table, said solvent being evaporated to use the condensed solution as the sample, the sample being positioned at a micro spectrometric analytical portion together with the sample table to be irradiated with infrared rays, and a spectrum reflected from said infrared ray-reflecting member through the sample being measured.

And, a further basic micro spectrometric analytical method according to the present invention is characterized in that a very small quantity of solution of a solute in a solvent is deposited drop by drop on a base made of water-repellent resins, said solvent being evaporated to be condensed, the condensed solution to be used as the sample being transferred to an infrared ray-reflecting material, the sample being positioned at a micro spectrometric analytical portion together with the infrared ray-reflecting material to be irradiated with infrared rays, and a spectrum reflected from the infrared ray-reflecting material through the sample being measured.

In addition, a still further basic micro spectrometric analytical method according to the present invention is characterized in that a very small quantity of solution of a solute in a solvent is deposited drop by drop on a thin film made of water-repellent resins of a sample table provided with the thin film mounted on an infrared ray-transmitting portion, the solvent being evaporated to use the condensed solution as the sample, the sample being positioned at a micro spectrometric analytical portion together with the sample table to be irradiated with infrared rays, and a spectrum, which is transmitted through the sample and the sample table, being measured.

Furthermore, a still further basic micro spectrometric analytical method according to the present invention is characterized in that a very small quantity of solution of a solute in a solvent is deposited drop by drop on a base made of water-repellent resins, the solvent being evaporated to be condensed, the condensed solution to be used as the sample being transferred to an infrared ray-transmitting material, the sample being positioned at a micro spectrometric analytical portion together with the infrared ray-transmitting material to be irradiated with infrared rays, and a spectrum, which is transmitted through the sample and the infrared ray-transmitting material, being measured.

In the above described respective inventions, the solution deposited drop by drop on a surface of the water-repellent resins is not only limited in diffusion thereof to hold a spherical shape by surface tension but also the diameter of the spherical shape is gradually reduced with evaporation of the solvent, whereby nonvolatile substances, that is, the solute, are coherently condensed, and a condensed sample having a reduced expansion and an increased thickness is obtained.

The condensed sample has an increased thickness. Thus, the infrared ray-absorbing intensity by the sample in the micro spectrometric analytical portion is heightened. As a result, the solution containing the solute can be analyzed in high sensitivity by an analytical method in which infrared rays reflected or transmitted through the solution are measured, even though a very small quantity of solution containing the solute is used as the sample.

In the present invention, in order to more progressively develop the above described basic micro spectrometric analytical methods, the following micro spectrometric analytical method has been proposed. That is to say, pinholes, which become condensing nuclei of the solution of the solute in the solvent, may be formed on the base made of the water-repellent resins at appointed intervals to deposit a very small quantity of solution drop by drop on portions where the pinholes have been formed, whereby the solution is condensed by evaporating the solvent.

In addition, pinholes, which become condensing nuclei of the solution of the solute in the solvent, may be formed on a thin film made of water-repellent resins of a sample table provided with the thin film mounted on an infrared ray-transmitting material at appointed intervals to deposit a very small quantity of solution drop by drop on portions where pinholes have been formed, whereby the solution is condensed by evaporating the solvent.

In the case where the pinholes are formed on the base made of water-repellent resins or on the thin film made of water-repellent resins of the sample table provided with the thin film mounted on the infrared ray-transmitting material in the above described manner, the solution deposited drop by drop on portions where the pinholes have been formed, of a surface of this fluoride family resin is not only limited in diffusion thereof to hold a spherical shape around the pinholes by surface tension, but also the solute is coherently condensed so that the diameter of the spherical shape may be gradually reduced with evaporation of the solvent with the pinholes as the condensing nuclei, and the condensed sample having a reduced expansion and an increased thickness is obtained with the solute arranged orderly at appointed positions with the pinholes as centers.

The condensed sample has an increased thickness and thus the infrared ray-absorbing intensity of the sample in the micro spectrometric analytical portion is heightened. As a result, the solution containing the solute can be analyzed in high sensitivity by an analytical method in which infrared rays reflected or transmitted through the solution are measured, even though a very small quantity of solution containing the solute is used as the sample. In addition, the condensed samples are arranged orderly with the pinholes as the centers, so that automation of the spectrometric analysis is also possible.

Furthermore, the surface of the thin film made of the water-repellent resins mounted on the infrared ray-reflecting material of the sample table may be irradiated with laser beams or ultraviolet rays at appointed intervals in place of formation of pinholes to reduce the surface tension of very small zones and then a very small quantity of solution of the solute in the solvent may be deposited drop by drop on these very small zones to condense the solution by evaporation of the solvent.

The surface of the base made of the water-repellent resins may also be irradiated with laser beams or ultraviolet rays at appointed intervals to reduce the surface tension of very small zones and then a very small quantity of solution of the solute in the solvent may be deposited drop by drop on the very small zones to condense the solution by an evaporation of the solvent.

If the very small zones (having an area of 20 $\mu m \times 20$ $\mu m$, for example) of the surface made of the water-repellent resins are irradiated with laser beams or ultraviolet rays in the above described manner, the surface of the resins is denatured by this irradiation to reduce the surface tension of the irradiated zones. The solution deposited drop by drop on the denatured very small zones is limited in diffusion by the surface tension of portions of the water-repellent resins surrounding the denatured very small zones and is condensed with the denatured very small zones as centers, whereby a relatively thick sample is formed. Accordingly, the sample can be provided in an orderly arrangement with the denatured very small zones as centers.

The infrared ray-absorbing intensity of the sample in the micro spectrometric analytical portion is heightened by using a relatively thick sample. As a result, the sample can be analyzed in high sensitivity by an analytical method in which reflected or transmitted infrared rays passing through the sample are measured, even though a very small quantity of minute sample is used. In addition, the samples are provided in an orderly arrangement with the denatured very small zones as centers, so that automation of the spectrometric analysis is also possible.

Furthermore, in the present invention, a method of detecting organic compounds by the use of the above described micro spectrometric analytical method is proposed. That is to say, a method of detecting organic compounds according to the present invention is characterized in that a liquid eluted from a column of a liquid chromatograph is deposited drop by drop on a thin film made of water-repellent resins and a sample of organic compounds coherently concentrated on the thin film is irradiated with infrared rays to detect reflected infrared rays obtained at that time and measure an absorbing degree of the reflected infrared rays, thereby detecting the presence of organic compounds and their concentration.

In this case, the liquid eluted from the column of the liquid chromatograph may be deposited drop by drop on the thin film made of water-repellent resins and the sample of organic compounds coherently concentrated on the thin film may be irradiated with infrared rays to detect transmitted infrared rays and measure the absorbing degree of the infrared rays, thereby detecting the presence of organic compounds and determining the concentration thereof.

According to the above described method of detecting organic compounds, the liquid eluted from the column of the liquid chromatograph is coherently condensed on the thin film made of the water-repellent resins to form a condensed sample having a reduced expansion and an increased thickness. This sample is irradiated with infrared rays to measure the absorbing degree of the infrared rays, whereby the presence and concentration of organic compounds can be detected.

In addition, in the present invention, there is proposed a method of making liquid flowing through one passage branch into two passages at a junction. That is to say, the method of making a liquid branch according to the present invention is characterized in that the respective outlet ends of two branched passages are relatively changed in height so that the ratio of the flow rate of a liquid flowing through one passage to that of a liquid flowing through the other passage may be changed.

In this method of making a liquid branch, in the case where, for example, the two branched passages are formed by tubes having a ratio of sectional areas of 1:4, the liquid flows through the respective branched passages in a flow rate corresponding to the ratio of sectional areas if the outlet ends of both branched passages are horizontal. However, if the outlet end of the branched passage having the larger diameter is lowered while keeping the outlet end of the branched passage having the smaller diameter horizontal, the liquid correspondingly flows through the branched passage having the larger diameter at a flow rate larger than that corresponding to the original ratio of sectional areas. On the contrary, if the outlet end of the branched passage having the smaller diameter is lowered while keeping the outlet end of the branched passage having the larger diameter horizontal, the liquid correspondingly flows through the branched passage having the smaller diameter at a flow rate larger than that corresponding to the original ratio of sectional areas.

BRIEF DESCRIPTION OF THE DRAWINGS

The basic micro spectrometric analytical methods according to the present invention are shown in FIGS. 1 to 9, in which

The micro spectrometric analytical methods progressively developed from the above described basic micro spectrometric analytical methods, more concretely the micro spectrometric analytical method with pinholes becoming condensing nuclei of a solution formed on a surface of a sample table, are shown in FIGS. 10 to 16, in which

The micro spectrometric analytical methods progressively developed from the above described basic micro spectrometric analytical methods, more concretely the micro spectrometric analytical method with denatured very small zones formed on the surface of a sample table, are shown in FIGS. 17 to 24, in which

The methods of detecting organic compounds by the use of the above described micro spectrometric analytical methods are shown in FIGS. 26 to 33, in which

FIG. 30(A) is a chromatogram obtained by an ultraviolet detector in conventional liquid chromatograph;

FIG. 30(B) is a chromatogram obtained by an ultraviolet detector in liquid chromatograph according to the present invention;

FIG. 30(C) is a chromatogram obtained by an infrared ray detector of a micro spectrometric analyzer according to the present invention;

DESCRIPTION OF THE PREFERRED EMBODIMENTS

First, the basic micro spectrometric analytical methods according to the present invention will be described.

Figure 1:
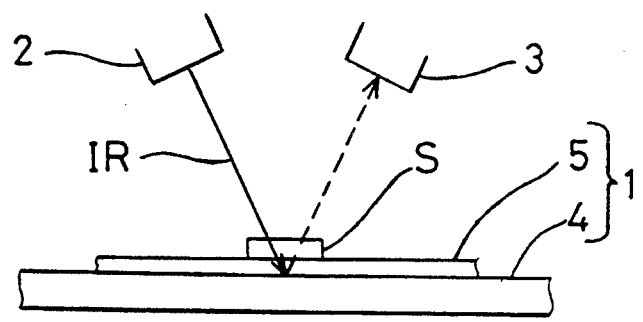
FIG. 1 is a diagram showing the principle of a micro spectrometric analytical method using reflection of infrared rays.

FIG. 1 is a diagram showing the principle of a micro spectrometric analytical method using reflection of infrared rays. Referring to FIG. 1, reference numeral 1 designates a sample table arranged in, for example, a micro spectrometric analytical portion of FTIR for holding a sample S.

Reference numeral 2 designates a light source for irradiating sample S on sample table 1 with infrared rays IR, reference numeral 3 designating a spectrum-measuring device for measuring the reflected spectrum of infrared rays IR from sample S, which is quantitatively or qualitatively determined by spectrum-measuring device 3 on the basis of measured information from the reflected spectrum.

The sample table 1 according to this preferred embodiment is provided with a thin film 5 made of fluoride resins rich in water-repellency of, for example, 25 μm in thickness (preferably 16 μm or 8 μm in order to reduce suppressed absorption of infrared rays) mounted on a mirror-finished portion of a mirror-finished metallic infrared ray-reflecting member 4. Spectrum-measuring device 3 measures the spectrum reflected by infrared ray-reflecting member 4 through sample S and thin film 5 made of fluoride resins.

The thin film 5 may be, for example, coated on an infrared ray-transmitting member (for example a crystal or film of alkali halide family materials, such as KBr and NaCl) to mount thin film 5 on infrared ray-reflecting member 4 through the infrared ray-transmitting member. In this case, if thin film 5 has pinholes, the pinholes are filled up with the infrared ray-transmitting member to effectively prevent a solution from soaking between thin film 5 and infrared ray-reflecting member 4.

Figure 2:
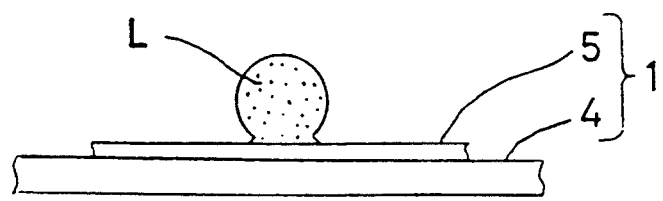
FIG. 2 is a diagram showing a solution deposited drop by drop on a sample table.

On the other hand, the sample S may be, for example, an eluted substance separated by liquid chromatograph and held on thin film 5, made of fluoride resins, which will be mentioned next. That is to say, a very small quantity of a solution L of a solute (which is used as the sample S, as described later) in a solvent is deposited drop by drop on thin film 5 by the use of an instrument such as a riffle sampler, as shown in FIG. 2.

Thin film 5 is rich in water-repellency, even in the case where, for example, methanol or ethanol is selected as the solvent, so that the solution deposited drop by drop on thin film 5 is limited in diffusion by surface tension to maintain a spherical shape.

Figure 3:
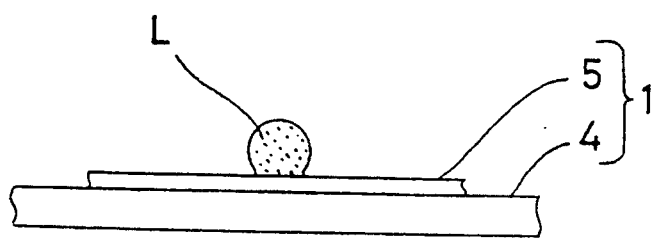
FIG. 3 is a diagram showing a solvent which is being evaporated from the solution.
Figure 4:
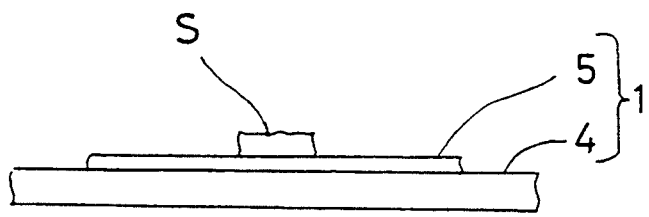
FIG. 4 is a diagram showing a condensed condition of the solution.

If the solvent in solution L is evaporated (naturally or forcibly by means of a heater and the like), as shown in FIG. 3., solution L is reduced in diameter while maintaining a spherical shape to coherently condense non-volatile substances and form a condensed sample S on thin film 5, as shown in FIG. 4.

Up to that time in the process this condensed sample S is relatively thick and has a reduced expansion due to limitation of diffusion of solution L. In this connection, in the case where 1 μl of solution L (10 μl of fluid paraffin in 100 ml of acetone) was deposited drop by drop on thin film 5, solution L exhibited a spherical shape and the solvent was evaporated from a circumferential portion of a spherical surface of solution L to form a relatively thick circular sample S having a diameter of about 100 μm.

Figure 5:
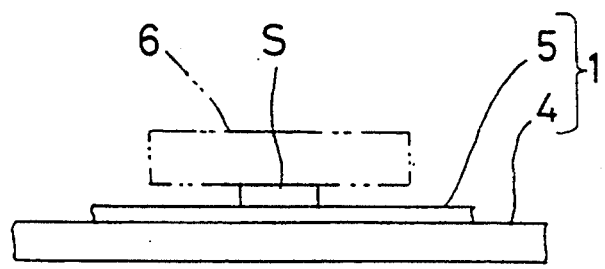
FIG. 5 is a diagram showing a condensed sample pressed so as to be flat.

This condensed sample S is positioned at a micro spectrometric analytical portion together with sample table 1 to carry out a micro spectrometric analysis. Preferably, condensed sample S is pressed by a suitable pressing means 6 to be flattened, as shown in FIG. 5, thereby improving the sensitivity of measurement.

Figure 25:
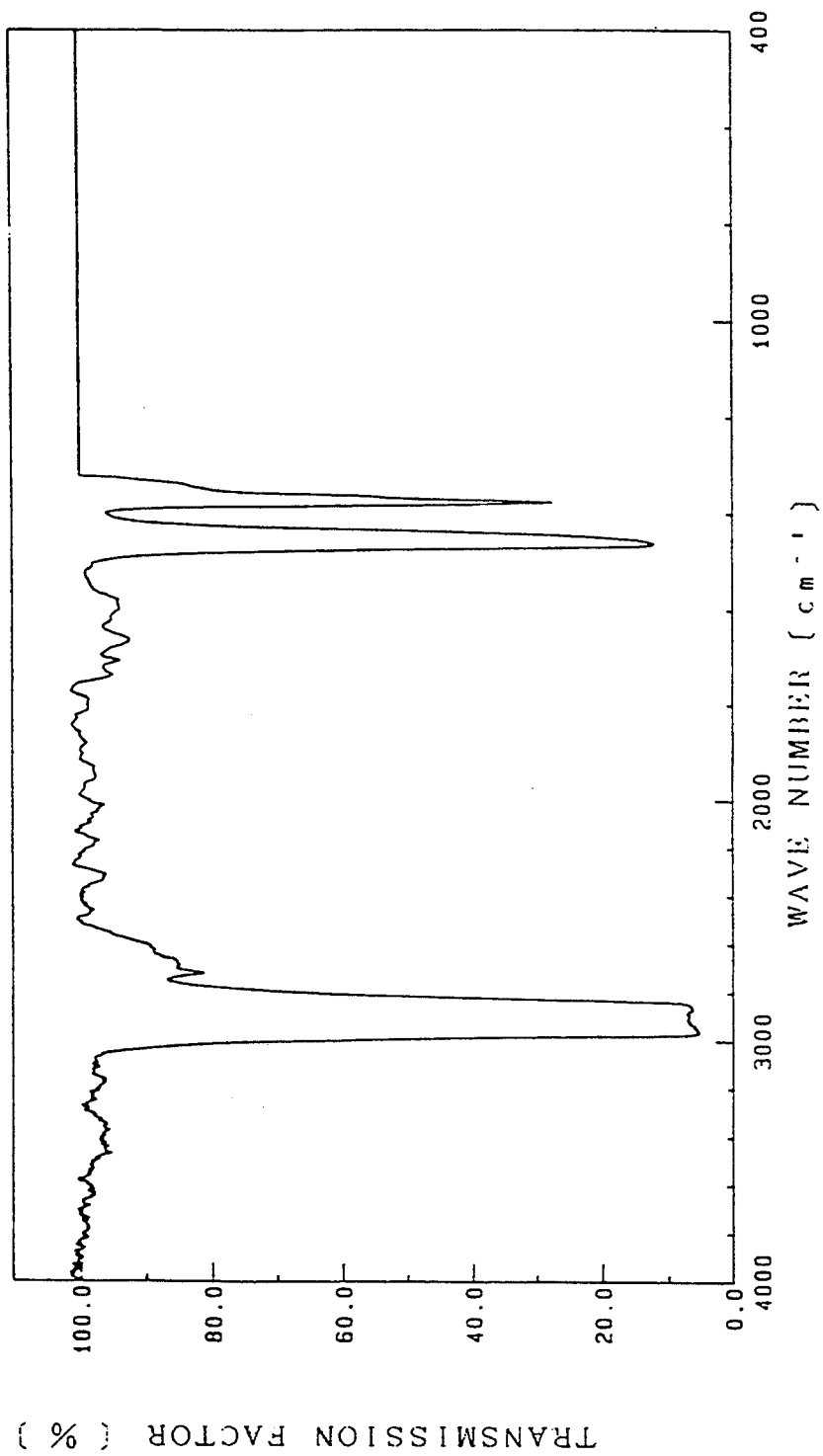
FIG. 25 is a diagram showing transmission characteristics of infrared rays obtained by the micro spectrometric analytical method according to the present invention.

The condensed sample S has considerable thickness, so that the infrared ray absorption intensity of sample S in the micro spectrometric analytical portion is heightened. Concretely speaking, a transmission factor of infrared rays measured by a microscopic FTIR/FT-530 (made by HORIBA, Ltd.) was about 10% at a wave number of about 1,450 cm$^{-1}$, as shown in FIG. 25. That is to say, the absorbing degree of light is remarkably high to an extent of 1.0, which is 100 times that in the already described conventional methods, so that the analysis of the sample by measuring the reflected spectrum can be achieved in high sensitivity (the sensitivity is improved 100 times as compared with the conventional methods).

In addition, the solvent in solution L may be forcibly evaporated by means of a heater and the like rather than evaporated naturally. At this time, if the solvent is evaporated at too high a rate, there is a possibility that the coherence of sample S is apt to be reduced and thus sample S is apt to be expanded, whereby the thickness of condensed sample S is reduced.

Figure 6:
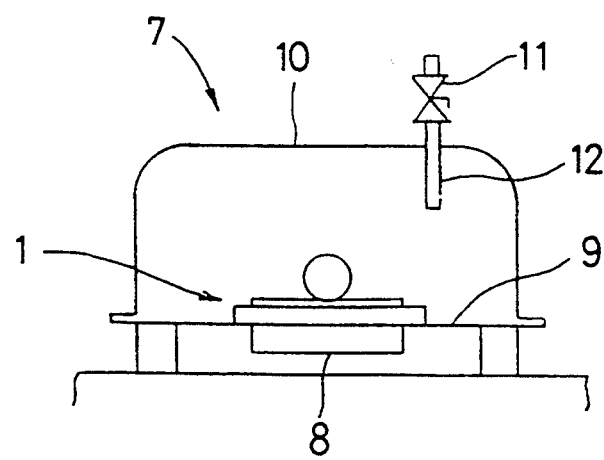
FIG. 6 is a sectional view showing control means for controlling the speed of evaporation of solvent.

Means 7 for controlling the rate of forcibly evaporating the solvent is shown in FIG. 6. Controlling means 7 comprises a trestle 9 provided with a heater 8 on a lower surface thereof and an airtight vessel 10 placed over trestle 9. Airtight vessel 10 is provided with a fine tube 12 with an exhaust-controlling valve 11 passing therethrough.

The above-described construction leads to the following advantages:

That is to say, not only can the solvent in solution L be evaporated under saturated conditions, but also the rate of evaporation of the solvent can be controlled by positioning sample table 1 on trestle 9 to deposit a very small quantity of solution L drop by drop on thin film 5 of sample table 1, placing airtight vessel 10 on trestle 9 so as to cover sample table 1 to generate heat from heater 8, and controlling the displacement by means of control value 11. Thus, not only can the concentricity of sample S be improved, but also solution L and thus condensed sample S can be prevented from being contaminated with the open air.

Figure 7:
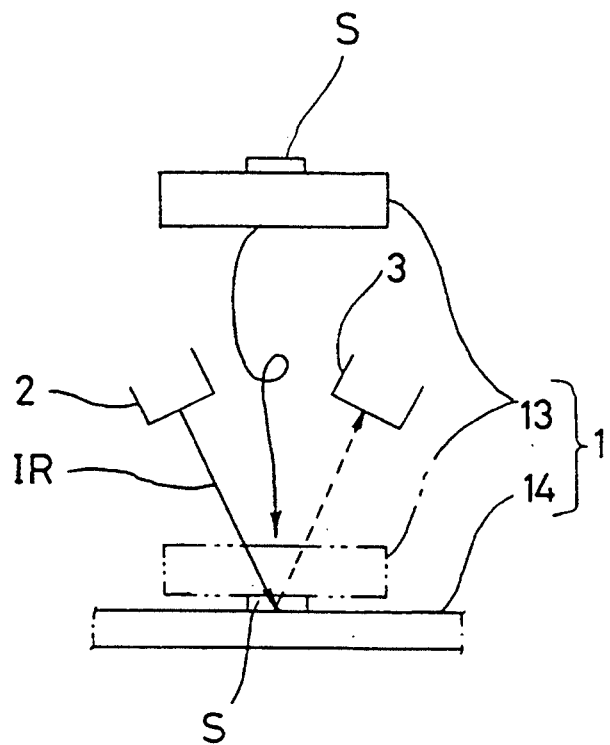
FIG. 7 is a diagram showing a sample table according to another preferred embodiment using reflection of infrared rays.

FIG. 7 shows a sample table 1 according to another preferred embodiment in an analytical method using reflection of infrared rays. In this embodiment sample table 1 comprises a base 13 made of fluoride resins and an infrared ray-reflecting member 14, to which condensed sample S on base 13 is transferred. In more detail, solution L is condensed upon base 13 by means shown in FIGS. 2 to 4, transferred to an infrared ray-reflecting member 14 having a mirror finished sample-holding surface, and positioned in a micro spectrometric analytical portion.

Such construction leads to the following advantages:

That is to say, infrared rays irradiated from light source 2 are absorbed by transferred sample S and reflected by infrared ray-reflecting member 14. The spectrum of the reflected infrared rays in measured by spectrum-measuring device 3. The sensitivity of measurement of the embodiment of FIG. 7 is improved as compared with the micro spectrometric analytical method shown in FIG. 1, due to the absence of thin film 5 in the path of infrared rays reflected from infrared ray-reflecting member 14 to sample S.

Figure 8:
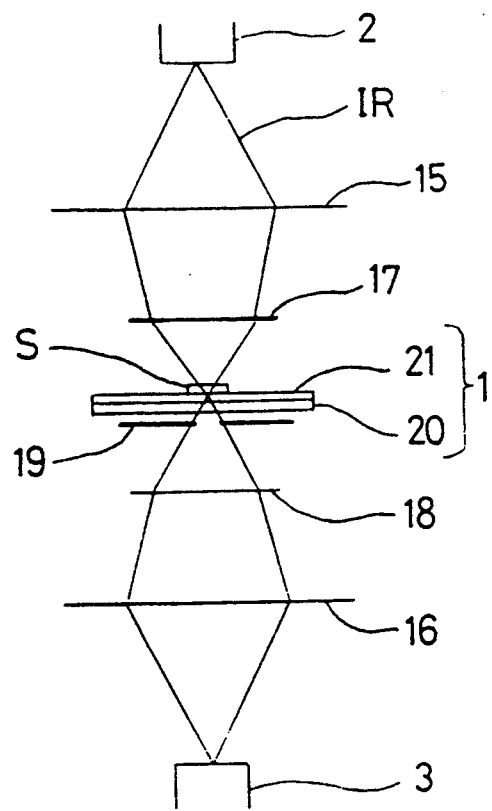
FIG. 8 is a diagram showing the principle of a micro spectrometric analytical method using transmission of infrared rays.

FIG. 8 is a diagram showing the principle of a micro spectrometric analytical method using transmission of infrared rays according to the present invention. Referring to FIG. 8, reference numerals 15, 16 designate a condensing mirror, reference numerals 17, 18 designate a beam condenser, and reference numeral 19 designates a mask. The sample is quantitatively or qualitatively determined by spectrum-measuring device 3 on the basis of measured information of the spectrum of infrared rays transmitted through sample S.

Beam condensers 17, 18 are provided to raise the condensing efficiency. However, the condensing efficiency can also be achieved by omitting beam condensers 17, 18 and instead placing a condensing lens midway of the incident light passage to sample S.

The sample table 1 in this preferred embodiment is formed of an infrared ray-transmitting member 20 made of, for example, a crystal of KBr, and provided with a thin film 21 made of fluoride resins. Infrared ray-transmitting member 20 is formed of materials highly transmissive to infrared rays, that is, a crystal or film made of alkali halide family materials, such as NaCl and $CaF_2$, in addition to KBr, preferably materials having a reduced solubility Furthermore, if there is no problem in respect of strength, sample table 1 may be composed merely of thin film 21, omitting infrared ray-transmitting member 20.

Figure 9:
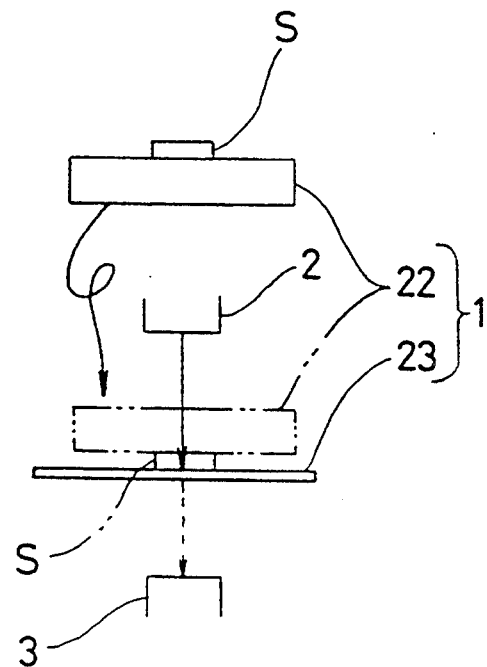
FIG. 9 is a diagram showing a sample table according to another preferred embodiment using transmission of infrared rays.

FIG. 9 shows a sample table 1 according to another preferred embodiment in an analytical method using transmission of infrared rays. Referring to FIG. 9, sample table 1 comprises a base 22 made of fluoride resins and an infrared ray-transmitting member 23, to which condensed sample S on base 22 is transferred. In more detail, sample table 1 comprises base 22 made of fluoride resins for condensing the solution L by means shown in FIGS. 2 to 4 and an infrared ray-transmitting member 23 formed of a crystal or film made of alkali halide family materials, such as KBr and NaCl, positioned in the micro spectrometric analytical portion, to which sample S is transferred.

According to such construction, infrared rays irradiated from light source 2 are absorbed by transferred sample S and transmitted through infrared ray-transmitting member 23. The spectrum of the transmitted infrared rays is measured by spectrum-measuring device 3. The sensitivity of measurement is improved as compared with the micro spectrometric analytical method shown in FIG. 8 due to the absence of thin film 21 in the path of infrared rays transmitted through sample S.

If desired, thin film 5 can be applied to infrared ray-reflecting member 4 or thin film 21 applied to infrared ray-transmitting member 20 by coating a dispersion of fluoride resins or sticking a fluoride resin film upon infrared ray-reflecting member 4 or infrared ray-transmitting member 20, respectively.

As above described, in the basic micro spectrometric analytical method according to the present invention, the solvent in solution L is evaporated under conditions such that diffusion is limited by water-repellent resins, such as fluoride resins, upon which solution L is deposited. The solute contained in solution L is thereby coherently condensed, whereby solution L is converted to sample S having substantial thickness and reduced expansion, and condensed sample S is subjected to micro spectrometric analysis by reflection or absorption of infrared rays. The thickness of sample S is remarkably increased compared to conventional methods and the infrared ray-absorbing intensity by sample S is increased. Thus, sample S can be analyzed in high sensitivity by either reflection or transmission of infrared rays according to the analytical method of the present invention even though a very small quantity of original minute solution L is used as the sample S.

Next, the methods, which have been achieved by progressively developing the above described basic micro spectrometric analytical method, will be separately described with reference to FIGS. 10 to 33.

At first, the invention, in which the pinholes becoming the condensing nuclei are formed on the thin film made of the fluoride resins of the sample table with the thin film made of the fluoride resins mounted on the base made of the fluoride resins or the infrared ray-transmitting member, will be described with reference to FIGS. 10 to 16.

Figure 10:
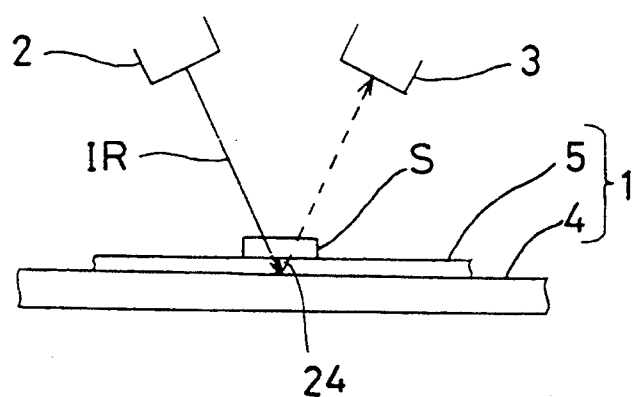
FIG. 10 is a diagram showing the principle of a micro spectrometric analytical method using reflection of infrared rays.
Figure 11:
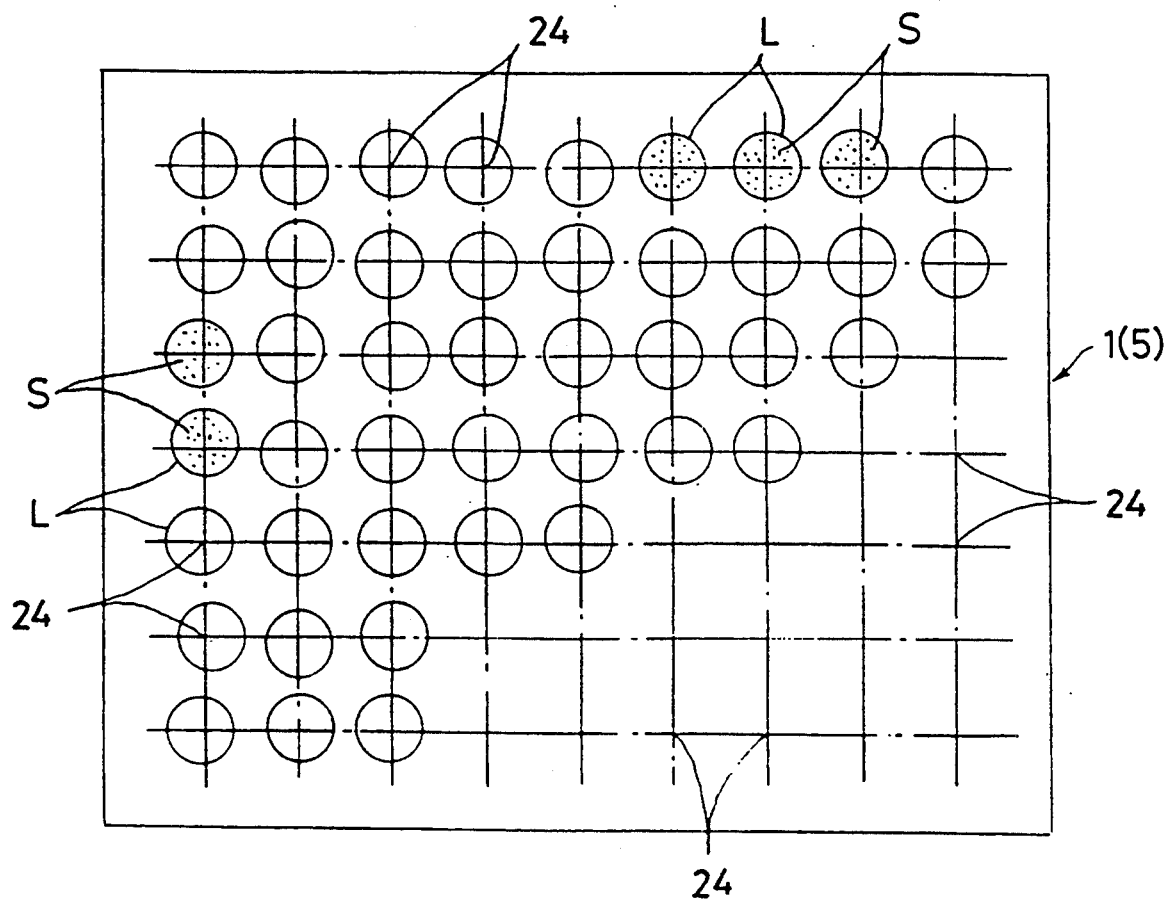
FIG. 11 is a diagram showing a solution deposited drop by drop on portions where pinholes are formed.

FIG. 10 is a diagram showing the principle of the micro spectrometric analytical method by the reflection of infrared rays in the present invention. Referring to FIG. 10, reference numeral 24 designates a large number of pinholes formed in the longitudinal and lateral directions of the thin film 5 made of the fluoride resins at appointed intervals on the thin film 5 made of the fluoride resins, as shown in FIG. 11. Although said pinholes 24 pass through the thin film 5 made of the fluoride resins in the preferred embodiment shown, they may have a concaved shape.

The pinholes 24 serve as the condensing nuclei of the solution L of the solute (for example an eluted substance separated by the liquid chromatograph) in a solvent such as methanol or ethanol. Concretely speaking, the pinholes 24 having diameters of 200 μm or less are formed at regular intervals of 5 mm by means of the pointed end of a gimlet.

In this preferred embodiment, the sample S is formed as follows:

A very small quantity of the solution L of the solute in the solvent is deposited drop by drop on portions, where the pinholes 24 are formed, of the thin film 5 made of the fluoride resins by the use of an instrument such as riffle sampler, as shown in FIG. 11.

Figure 12:
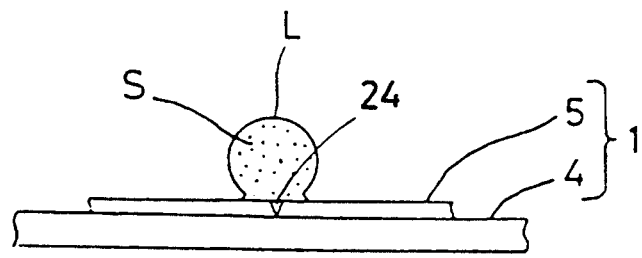
FIG. 12 is a diagram showing a solution deposited drop by drop on a sample table.

At this time, the thin film 5 made of the fluoride resins is rich in water-repellency even in the case where for example methanol or ethanol is selected as the solvent, so that he solution deposited drop by drop on the thin film 5 made of the fluoride resins is limited in diffusion thereof to keep a spherical shape by a surface tension thereof, as shown in FIG. 12.

In addition, it is preferable that a quantity of the solution L deposited drop by drop is regulated so that a diameter of the solution L, to which a spherical shape has been given when deposited drop by drop, may amount to about 2 mm.

Figure 13:
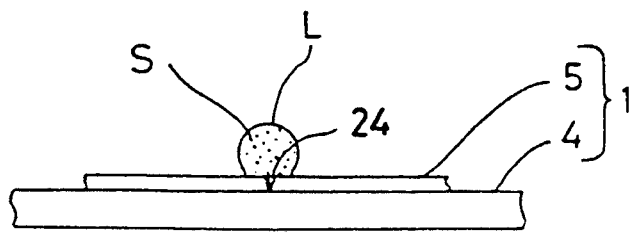
FIG. 13 is a diagram showing a solvent which is being evaporated from a solution.
Figure 14:
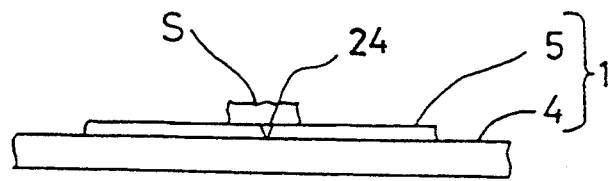
FIG. 14 is a diagram showing the condensed condition of a sample.

And, as shown in FIG. 13, when the solvent in the solution L is evaporated (naturally or forcibly by means of a heater and the like), the solution L is reduced in diameter with keeping the spherical shape thereof to condense nonvolatile substances, that is the solute, and at last, as shown in FIG. 14, the condensate (sample S) composed of merely the solute is formed on the thin film 5 made of the fluoride resins.

Figure 15:
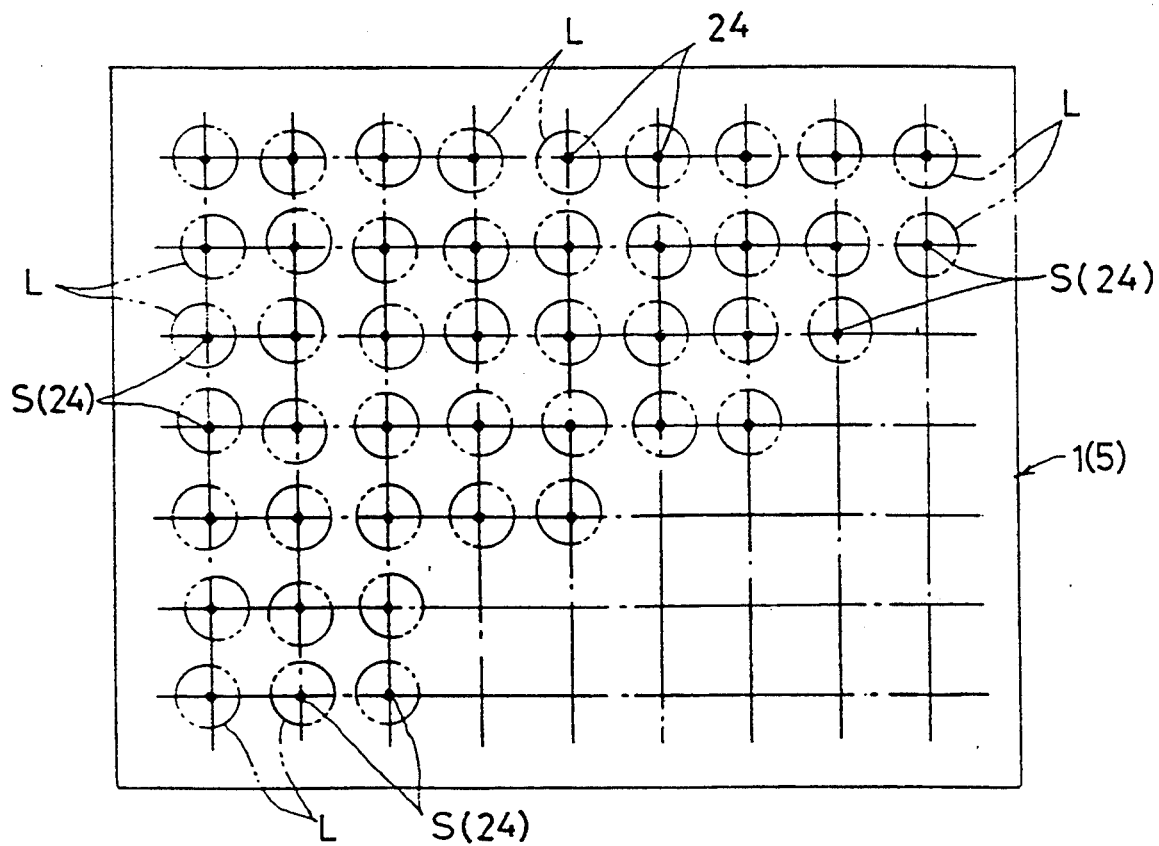
FIG. 15 is a plan view showing the condensed condition of a sample on a sample table.

In the condensation of the solution L, the solution L is condensed so as to be attracted to the pinholes by a surface tension thereof with the pinholes 24 exhibiting a less solid surface tension as centers, so that, as shown in FIGS. 11 and 15, the condensed sample S is orderly formed around centers of the pinholes 24 even though centers of the solution L deposited drop by drop on said portions, where the pinholes 24 have been formed, of the thin film 5 made of the fluoride resins are shifted form said centers of the pinholes 24. This is advantages for an automation of the spectrometric analysis of the sample S.

This condensed sample S has a thickness and a reduced expansion due to said limitation of the solution L in diffusion in a process up to that time. In this connection, in the case where 1 μl of the solution L of 10 μl of fluid paraffin in 100 ml of acetone was deposited drop by drop on the thin film 5 made of the fluoride resins, the solution L exhibited a spherical shape and the solvent was evaporated from the surface of the solution L to form the circular sample S having a thickness and a diameter of about 100 μm.

It goes without saying that it is preferable to pressedly flatten also this condensed sample S by means of the suitable means shown in FIG. 5, whereby improving the sensitivity of measurement.

This condensed sample S was measured on the transmission factor of infrared rays by the microscopic FTIR/FT-530 (made by HORIBA, Ltd.) with the results similar to those shown in FIG. 25.

In addition, the solvent in the solution L may be forcibly evaporated by means of said heater and the like other than by a natural evaporation. At this time, if the solvent is evaporated in a too high speed, there is the possibility that a coherence of the sample S is apt to be delayed and thus the sample S is apt to be expanded, whereby reducing the condensed sample S in thickness. Accordingly, it goes without saying that the means 7 for controlling the evaporating speed shown in FIG. 6 may be used.

Figure 16:
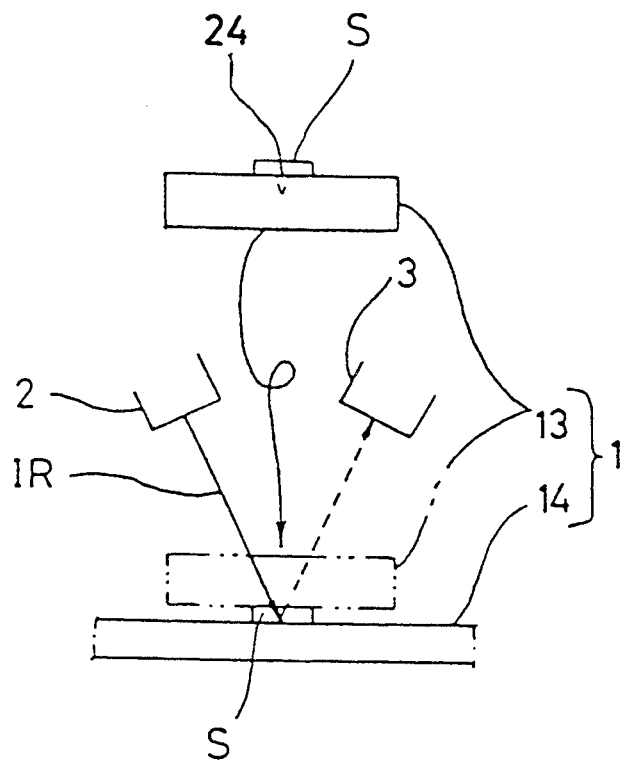
FIG. 16 is a diagram showing a sample table according to another preferred embodiment using reflection of infrared rays.

Next, FIG. 16 shows a sample table 1 according to another preferred embodiment used in the analytical method by the reflection of infrared rays but said sample table 1 is different from the sample table 1 show in FIG. 7 merely in that pinholes 24 serving as condensing nuclei of the solution L are formed on a base 13 made of fluoride resins at appointed intervals. In addition, in the case where a thickness was given to said base 13, it is preferable that said pinholes 24 are formed in concaved shape.

With such the construction, infrared rays IR irradiated from the light source 2 are absorbed by the transferred sample S and reflected by the infrared ray-reflecting member 14 and a spectrum of the reflected infrared rays is measured by the spectrum-measuring device 3, so that an advantage occurs in that a sensitivity of measurement can be improved as compared with the micro spectrometric analytical method shown in FIG. 10 due to an absence of the thin film 5 made of the fluoride resins in a reflecting surface portion of infrared rays.

And, it goes without saying that the micro spectrometric analytical method by the transmission of infrared rays may be used also in the preferred embodiment, in which the pinholes 24 serving as said condensing nuclei of the solution L are formed, and the apparatus is similar to that shown in FIG. 8 or FIG. 9, so that its detailed description is omitted.

As above described, in the micro spectrometric analytical method according to the present invention, the solvent in the solution L is evaporated under the condition that the diffusion is limited by the resins, such as fluoride resins, rich in water-repellency to coherently condense the solute contained in the solution L with the pinholes 24 as centers, whereby the solution L is turned into the sample S having a thickness and a reduced expansion, and the condensed sample S is subjected to the micro spectrometric analysis by the reflection or transmission of infrared rays, so that the thickness of the sample S can be remarkably increased as compared with the conventional methods and the infrared ray-absorbing intensity by the sample S can be increased and thus the sample S can be analyzed in high sensitivity by the analytical method by the reflection or transmission of infrared rays even though a very small quantity of original minute solution L is used as the sample S.

Moreover, the condensed samples S are orderly arranged with the pinholes 24 as centers, so that it is easily possible also to automate the spectrometric analysis, or, a small spherical shape is given to the solution L, so that the solution L is difficultly brought into contact with other solutions L or the sample S even though portions, where the solution L is deposited drop by drop, are brought close to each other and thus the solution L can be deposited drop by drop on more points as compared with a size of the sample table 1.

In addition, with the sample table I according to the present invention, the samples suitable for using in the above described methods, that is the condensed samples S having a thickness and a reduced expansion, can be formed so as to be orderly arranged at appointed positions.

Next, the invention, in which the surface of the thin film made of the fluoride resins mounted on the infrared ray-reflecting member of the sample table or the base made of the fluoride resins is irradiated with laser beams or ultraviolet at appointed intervals to reduce a surface tension of very small zones and then a very small quantity of solution of the solute in the solvent is deposited drop by drop on said very small zones to condense the solution by an evaporation of the solvent, is described with reference to FIGS. 17 to 24.

Figure 17:
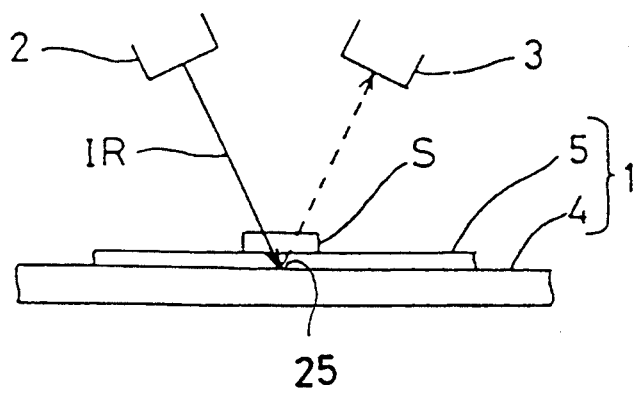
FIG. 17 is a diagram showing the principle of a micro spectrometric analytical method using reflection of infrared rays.

FIG. 17 is a diagram showing a principle of the micro spectrometric analytical method by the reflection of infrared rays according to the present invention. Referring to FIG. 17, reference numeral 25 designates a very small denatured zone formed on the thin film 5 made of the fluoride resins of the sample table 1. That is to say, a plurality of very small denatured zones (of for example 20 μm × 20 μm) denatured to be reduced in surface tension are formed at appointed intervals in the longitudinal and lateral directions on the thin film 5 made of the fluoride resins as shown exaggerated in FIG. 18. These very small denatured zones 25 are formed by, for example, irradiating with eximer laser beams by a mask-imaging method.

Figure 19:
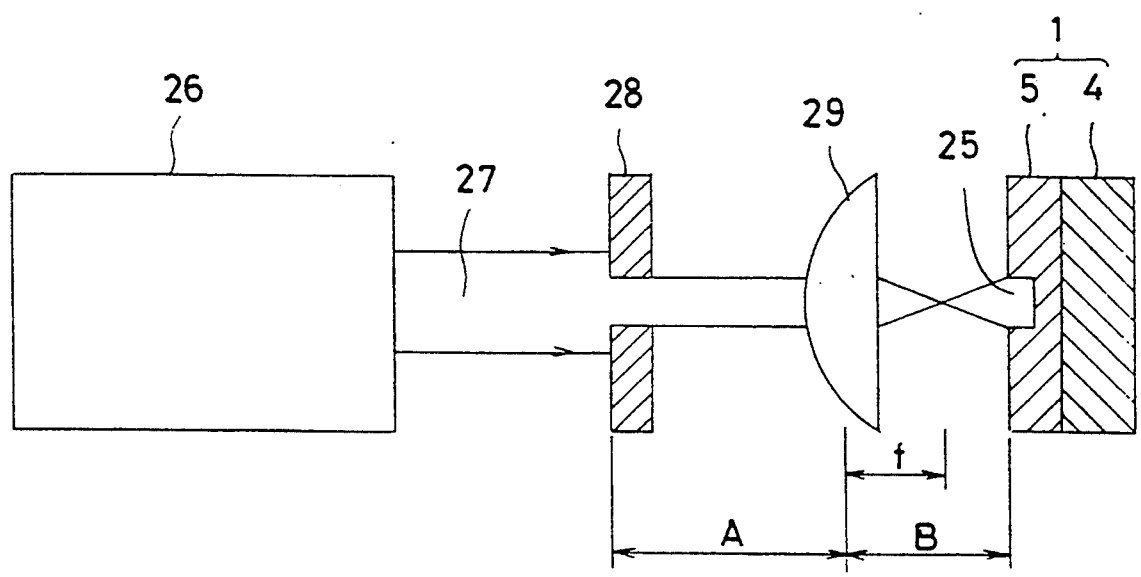
FIG. 19 is a diagram showing one example of apparatus for putting a mask-imaging method into practice.

FIG. 19 shows one example of apparatus for putting said mask-imaging method into practice. Referring to FIG. 19, reference numeral 26 designates an eximer laser emitting pulse-shaped exima laser beams 27, reference numeral 28 designating a mask with a suitable processing pattern formed thereon by etching, and reference numeral 29 designating a lens for condensing the exima laser beams 27, which have been transmitted through said mask 28, to project them on the thin film 5 made of the fluoride resins of he sample table 1.

And, provided that a distance from the mask 28 to said lens 29 is A, a distance from the lens 29 to the thin film 5 made of the fluoride resins being B, and a focal distance of the lens 29 being f.

$$1/A + 1/B = 1/f$$

holds good on the basis of the Gaussian theorem. At this time, a contraction factor is M expressed by the following equation:

$$M = A/B$$

In addition, at this time, provided that a density of energy of the eximer laser beams 27 on the mask 28 is $E_1$, a density of energy $E_2$ of the eximer laser beams 27 on the thin film 5 made of the fluoride resins is expressed by the following equation:

$$E_2 = M^2 E_1$$

Upon irradiating with the eximer laser beams 27 with using the above described apparatus and setting the above described A, B, f and $E_1$ to suitable values, the thin film 5 made of the fluoride resins of the sample table 1 is nonthermally processed (abraded) to denature a surface thereof with portions irradiated with the eximer laser beams 27 as centers, whereby forming very small denatured zones 25 with the reduced surface tension at suitable intervals.

In this case, also circumferential portions of the zones directly irradiated with the eximer laser beams 27 are influenced. That is to say, said surface is changed merely in a mask portion as observed by an optical microscope. In addition, a change is not observed by the microscopic FTIR between the circumferential portions and the fluoride resins not irradiated with the eximer laser beams 27 in infrared spectrum. And, when 1 μl of the solution L containing the solute in the form of liquid (for example the solute is Triton and the solvent is acetonitril) is deposited drop by drop on the fluoride resins, a diameter of the sample after the evaporation of the solvent amounted to 30 μm.

Figure 20:
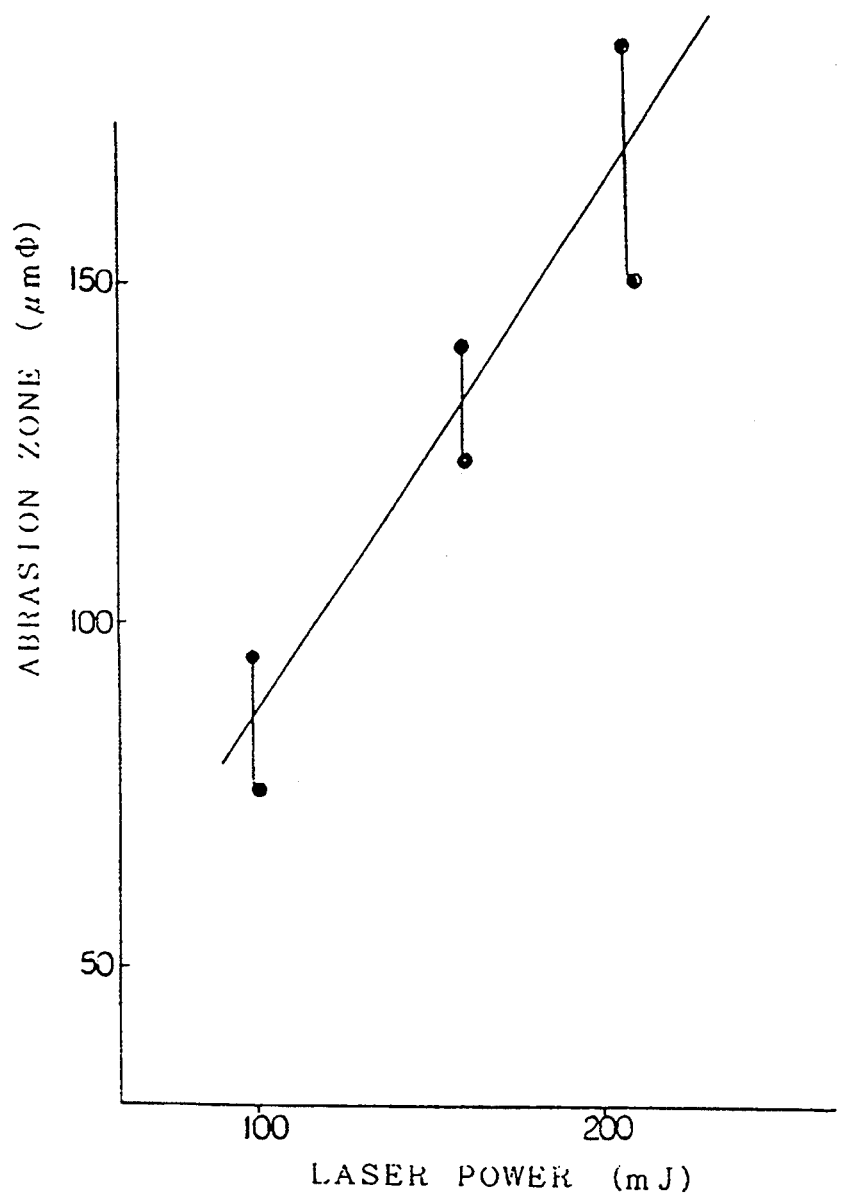
FIG. 20 is a diagram showing the relation between the power of laser beams applied and the abrasion zone.

It has been found that if a power of the laser beams irradiated is increased, a range influenced by the irradiation with the laser beams is increased, as shown in FIG. 20. In addition, if the mask to be irradiated with the laser beams was increased in size, also said range influenced by the irradiation with the laser beams was increased up to about 7 times the size of the mask. Furthermore, a difference resulting from a film-thickness of the thin film 5 made of the fluoride resins was not observed.

Besides, the very small denatured zones 25 may be formed by irradiating with $CO_2$ laser beams or YAG laser beams. Also ultraviolet rays may be applied.

Figure 18:
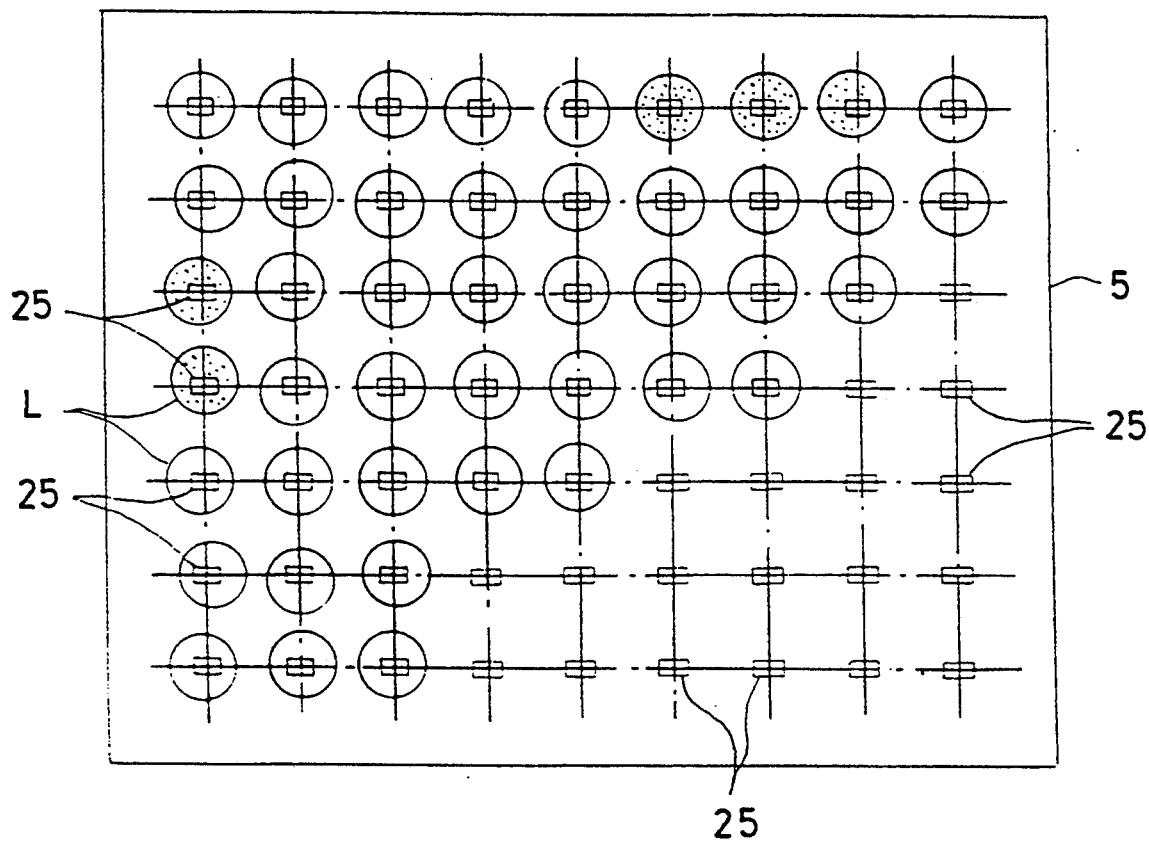
FIG. 18 is a plan view showing a solution L deposited drop by drop on denatured very small zones.
Figure 21:
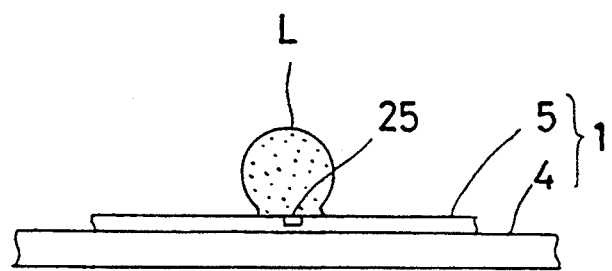
FIG. 21 is a diagram showing a solution deposited drop by drop on a sample table.

A very small quantity of the solution L of the solute in the solvent is deposited drop by drop on the very small denatured zones 25 on the thin film 5 made of the fluoride resins by the use of an instrument such as riffle sampler, as shown in FIG. 18. At this time, even in the case where for example methanol or ethanol is used as the solvent, the solution L deposited drop by drop on the thin film 5 made of the fluoride resins is limited in diffusion thereof due to a rich water-repellency of the thin film 5 made of the fluoride resins to keep the spherical shape by a surface tension thereof, as shown in FIG. 21. In this case, it is preferable that a quantity of the solution L deposited drop by drop is regulated so that a diameter of the solution L, to which a spherical shape is given when deposited drop by drop, may amount to for example about 2 mm.

Figure 22:
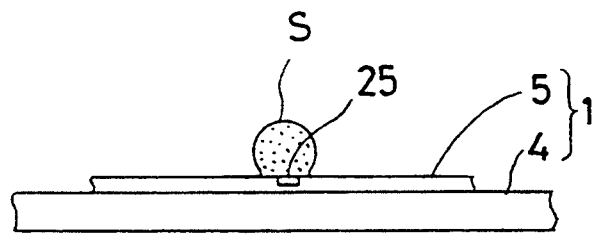
FIG. 22 is a diagram showing a solution which is being evaporated.

And, when the solvent in the solution L is evaporated naturally or forcibly by means of a heater and the like, the solution L is condensed with keeping the spherical shape thereof to form the condensed sample S composed of nonvolatile substances on the thin film 5 made of the fluoride resins, as shown in FIG. 22.

Figure 23:
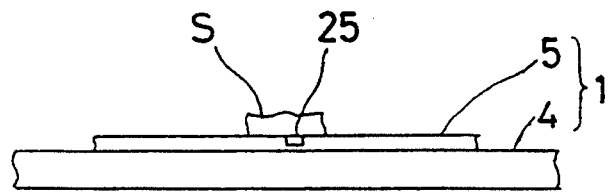
FIG. 23 is a diagram showing the condensed condition of a sample on a sample table.

In the condensation of the solution L, the solution L is condensed so as to be attracted to the very small denatured zones 25 with the very small denatured zones 25 as centers to be orderly formed with the very small denatured zones as centers, as shown in FIG. 23, without being influenced by small foreign matters existing in the very small denatured zones according to circumstances. This is advantageous for an automation of the spectrometric analysis.

This condensed sample S has a thickness and a reduced expansion due to said limitation of the solution L in diffusion in a process up to that time. In this connection, in the case where 1 μl of the solution 1 of 10 μl of fluid paraffine in 100 ml of acetone was deposited drop by drop on the thin film 5 made of the fluoride resins, the solution L exhibited a spherical shape and the solvent was evaporated from a circumferential portion of a spherical surface of the solution L to form a disk-shaped sample having a substantial thickness and a diameter of about 100 μm.

This condensed sample S was measured on the transmission factor of infrared rays by the microscopic FTIR/FT-530 (made by HORIBA, Ltd.) with the results similar to those shown in FIG. 25.

It goes without saying that is preferable to pressedly flatten also this condensed sample S by means of the suitable means 6 shown in FIG. 5, whereby improving the sensitivity of measurement.

In addition, the solvent in the solution L may be forcibly evaporated by means of said heater and the like other than by a natural evaporation. At this time, if the solvent is evaporated in a too high speed, there is the possibility that a coherence of the sample S is apt to be delayed and thus the sample S is apt to be expanded, whereby reducing the condensed sample S in thickness. Accordingly, it goes without saying that the means 7 for controlling the evaporating speed shown in FIG. 6 may be used.

Figure 24:
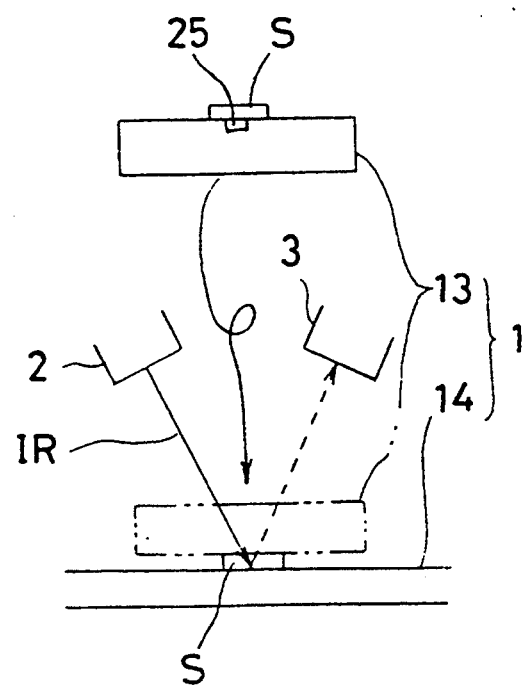
FIG. 24 is a diagram showing a sample table according to another preferred embodiment using reflection of infrared rays.

FIG. 24 shows another preferred embodiment of a sample table used in the analytical method by the reflection of infrared rays. A sample table 1 in this preferred embodiment comprises a base 13 made of fluoride resins with the very small denatured zones 25 formed at appointed intervals and an infrared ray-reflecting member 14 with a mirror-finished sample-holding surface transferredly holding the condensed sample S on said base 13 as the transferred sample and positioned in the micro spectrometric analytical portion.

With such the construction, infrared rays IR irradiated from the light source 2 are absorbed by the sample S and reflected by the infrared ray-reflecting member 14 and a spectrum of the reflected member 14 and a spectrum of the reflected infrared rays is measured by the spectrum-measuring device 3, so that an advantage occurs in that a sensitivity of measurement can be improved by an extent due to an absence of the thin film 5 made of the fluoride resins in a reflecting surface portion of infrared rays as compared with the micro spectrometric analytical method shown in FIG. 17.

And, it goes without saying that the micro spectrometric analytical method by the transmission of infrared rays may be used also in the preferred embodiment, in which the surface of the thin film 5 made of the fluoride resins or the surface of the base 13 made of the fluoride resins is irradiated with the laser beams or the ultraviolet rays at appointed intervals to reduce the surface tension of the very small denatured zones, and the apparatus is similar to that shown in FIG. 8 or FIG. 9, so that its detailed description is omitted.

As above described, in the micro spectrometric analytical method according to the present invention, the solvent in the solution L is evaporated under the condition that the diffusion is limited by the resins, such as fluoride resins, rich in water-repellency to coherently condense the solute contained in the solution L with the very small denatured zones 25 as centers, whereby the solution L is turned into the sample S having a thickness and a reduced expansion, and the condensed sample S is subjected to the micro spectrometric analysis by the reflection or transmission of infrared rays, so that the thickness of the sample S can be remarkably increased as compared with the conventional methods and the infrared ray-absorbing intensity by the sample S can be increased and thus the sample S can be analyzed in high sensitivity by the analytical method by the reflection or transmission of infrared rays even though a very small quantity of original solution L is used as the sample S.

The samples S are orderly arranged with the very small denatured zones 25 as centers, so that it is easily possible to automate the spectrometric analysis. In addition, a small spherical shape is given to the solution L, so that the solution L is difficultly brought into contact with other solutions L or the condensed sample S even though portions, where the solution L is deposited drop by drop, are brought close to each other and thus the solution L can be deposited drop by drop on more points as compared with a size of the sample table 1.

In addition, with the sample table 1 according to the present invention, the samples suitable for using in the above described methods, that is the condensed samples S having a thickness and a reduced expansion, can be formed so as to be orderly arranged at appointed positions.

Next, the method, in which organic compounds are detected by the above described micro spectrometric analytical method, is described with reference to FIGS. 26 to 33.

Figure 26:
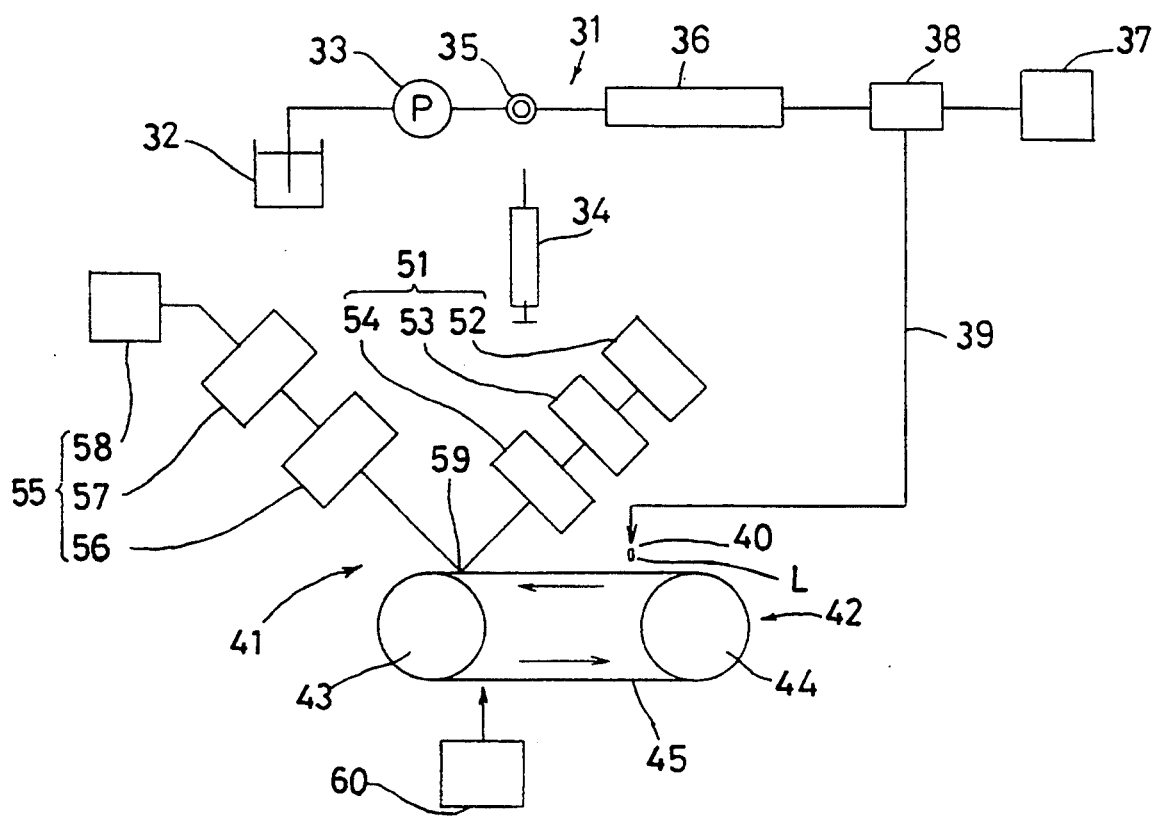
FIG. 26 is a diagram roughly showing one example of a construction of an apparatus for detecting organic compounds by the use of the above-described micro spectrometric analytical method.

At first, referring to FIG. 26, reference numeral 31 designates a liquid chromatograph comprising an eluted liquid tank 32, a pump 33, a sample injector 35 provided with a syringe 34, a column 36, an ultraviolet ray detector 37 and the like. Reference numeral 38 designates a device for making a liquid branch provided between said column 36 and said ultraviolet ray detector 37 for dividing a liquid eluted from the column 36 into the ultraviolet ray detector 37 and a micro spectrometric analyzer 41, which will be mentioned later, at a suitable shunting ratio (for example 19:1). Reference numeral 39 designates an eluted liquid passage connected with said device for making a liquid branch 38. Said eluted liquid passage 39 is provided with a dropping device 40 (refer to FIG. 27) at a pointed end thereof. In addition, the ultraviolet ray detector 37 is connected with a data-operating portion such as computer (not shown).

Figure 27:
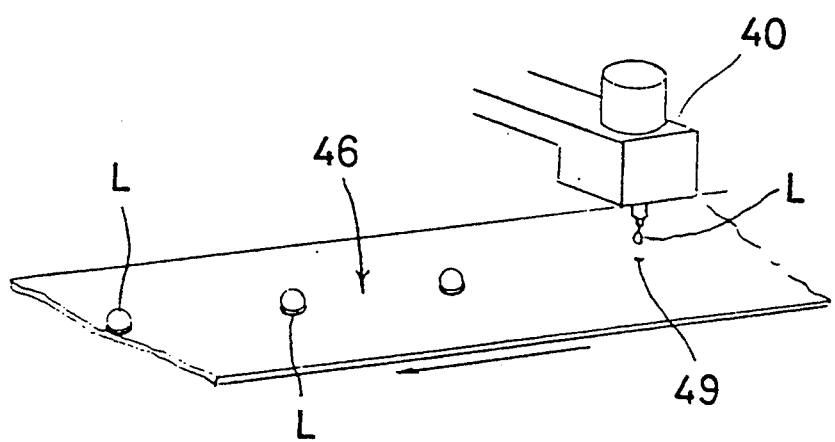
FIG. 27 is a perspective view showing one example of the sample table in the above-described apparatus.
Figure 28:
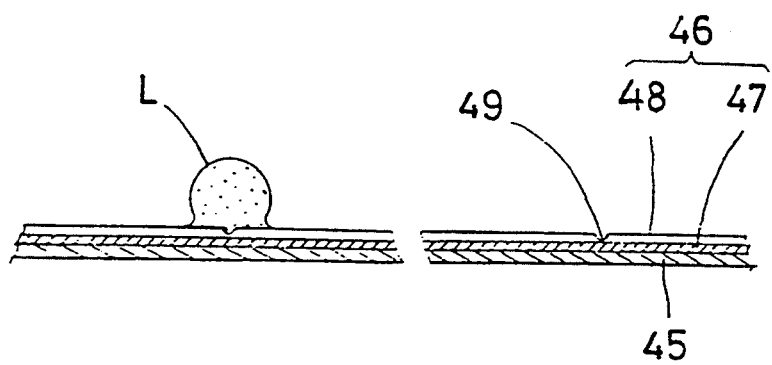
FIG. 28 is a sectional view showing the sample table.

Reference numeral 41 designates said micro spectrometric analyzer which has the following construction: At first, reference numeral 42 designates a sampler comprising an endless conveying belt 45 extended over a driving pulley 43 and a trailing pulley 44 and moving in an appointed direction at an appointed speed and a sample table 46 fixedly mounted on an upper surface of conveying belt 45 (refer to FIG. 27). Sample table 46 comprises a sampling plate 47 fixed on the upper surface of the conveying belt 45, as shown in FIG. 28, and a thin film 48 made of fluoride resins formed on an upper surface of said sampling plate 47.

In this preferred embodiment, the sampling plate 47 is formed of a thin stainless steel plate of for example about 100 $\mu$m thick so as to reflect infrared rays. In addition, said thin film 48 made of said fluoride resins is formed by forming for example fluoride resins rich in water-repellency in the thickness of for example about 0.1 $\mu$m. And, this thin film 48 made of the fluoride resins is provided with pinholes 49 having diameters of about 200 $\mu$m (or less) formed at suitable intervals (for example 8 to 10 mm) on an upper surface thereof by means of for example a pointed end of gimlet.

Now, provided that the eluted liquid is discharged from the column 36 of the liquid chromatograph 31 in a quantity of 1 ml/min and said shunting ratio between the side of the ultraviolet ray detector 37 and the side of the micro spectrometric analyzer 41 of the device for making a liquid branch 38 is 19:1, the eluted liquid flows through the eluted liquid passage 39 in a quantity of 50 $\mu$l/min. And, provided that a volume of one drop of the solution L deposited drop by drop from a dropping device 40 is 10 $\mu$l, 5 drops of the solution L are deposited drop by drop on the sample table 46 every minute. So, it is sufficient to move the conveying belt 45 in the direction shown by an arrow in FIG. 27 at a speed of 50 mm/min. Thus, the solution L is deposited drop by drop on said pinholes 49 on the sample table 46, as shown in FIGS. 27 and 28.

Figure 29A:
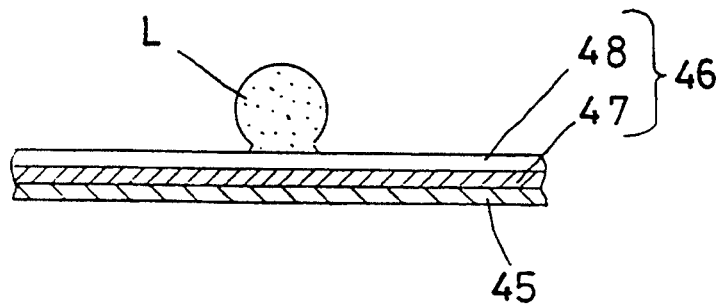
FIGS. 29(A)–29(C) are diagram schematically showing a process of coherently condensing a solution on the sample table.
Figure 29B:
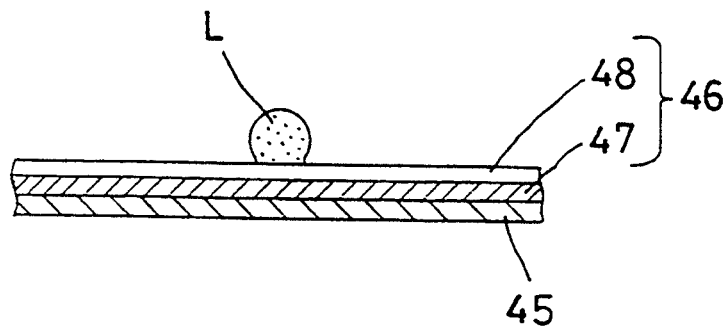
Figure 29C:
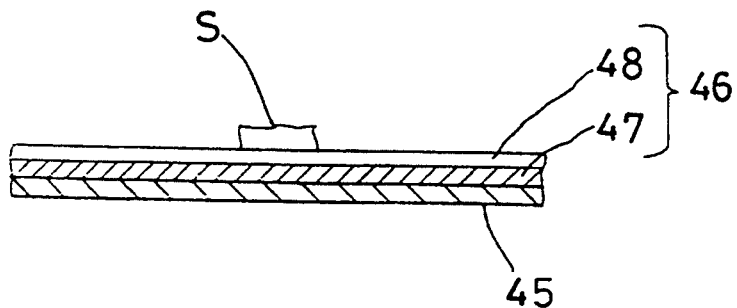

The drop-shaped solution L deposited on positions of the pinholes 49 on the thin film 48 made of the fluoride resins rich in water-repellency of the sample table 46 is limited in diffusion thereof to keep a spherical shape by a surface tension thereof, shown in FIG. 29(A). And, when the solvent in the solution L evaporated naturally or forcibly by means of a heater (not shown) the solution L is condensed with keeping said spherical shape to be reduced in diameter, as shown in FIG. 29(B), and at last turned int a coherently condensed sample S, as shown in FIG. 29(C). In short, the solution L deposited drop by drop on the thin film 48 made the fluoride resins is coherently condensed with the pinholes serving as the condensing nuclei formed in the thin film 48 made of the fluoride resins as centers to be turned into said samples S.

An apparatus, in which the sample S coherently condensed on the sample table 46 in the above described manner is irradiated with infrared rays and reflected infrared rays are detected, is described. Referring to FIG. 26 again, reference numeral 51 designates an infrared ray-irradiating portion comprising an infrared light source 52, a filter 53, a condensing portion 54 and the like. In addition, reference numeral 55 designates an infrared ray-detecting portion comprising a condensing portion 56, an infrared ray detector 57, an amplifier 58 and the like. Furthermore, said amplifier 58 is connected with said data-operating portion on the output side thereof in the same manner as the ultraviolet ray detector 37. Besides, referring to FIG. 26, reference numeral 59 designates a position irradiated with infrared rays and reference numeral 60 designates a device for rinsing the sample table 46.

In operation, at first, in the liquid chromatograph 31, the eluted liquid within the eluted liquid tank 32 is supplied to said sample injector 35 by means of said pump 33 and a sample liquid is introduced into the sample injector 36 by means of said syringe 34. And, said sample is introduced into the column 36 together with the eluted liquid to be subjected to an appointed separating treatment. And, the greater part of the eluted liquid discharged from the column 36 arrives at the ultraviolet ray detector 37 through the device for making a liquid branch 38 to put out a chromatogram, which will be mentioned later, from the ultraviolet ray detector 37.

On the other hand, a part of the eluted liquid enters said eluted liquid passage 39 through the device 38 for dividing for micro-liquid flow to arrive at said dropping device 40 through the eluted liquid passage 39. And, this eluted liquid is deposited drop by drop on the sample table 46 by means of the dropping device 40 to be conveyed to said position 59 to be irradiated with infrared rays by means of the conveying belt 45. And, as above described, the eluted liquid is evaporated till it arrives at the position 59 to be irradiated with infrared rays of the micro spectrometric analyzer 41 to be turned into the coherently condensed sample S having an appointed shape. This sample S is irradiated with infrared rays incident upon the sample S pass through the sample S and reflected by the sampling plate 47 below the sample S. The reflected infrared rays are incident upon said infrared ray detector 57 through said condensing portion 56. Thus, a spectrum of the infrared rays, which have passed through the sample S and the thin film 48 made of the fluoride resins and reflected by the sampling plate 47, is measured to put out also a chromatogram, which will be mentioned later, from the infrared ray detector 57.

The sample S on the sample table 46 is irradiated with infrared rays in the above described manner but the sample table 46 with the sample S, which has been irradiate with infrared rays, placed thereon arrives at said rinsing device 60 by means of the conveying belt 45 moving in the direction shown by said arrow in FIG. 26 to be rinsed by means of the rinsing device 60, whereby preparing for the following falling of the solution L drop by drop.

FIG. 30 shows chromatograms according to the conventional methods and those in the methods according to the present invention in comparison. FIG. 30(A) shows said chromatogram obtained by the ultraviolet ray detector of the conventional liquid chromatograph, FIG. 30(B) said chromatogram obtained by the ultraviolet ray detector 37 of the liquid chromatography 31 according to the present invention, and FIG. 30(C) said chromatogram obtained by the infrared ray detector 57 of the micro spectrometric analyzer 41 according to the present invention.

Now, provided that 5 substances A to E are contained in the eluted liquid and merely said substance B does not absorb ultraviolet rays, according to the conventional methods, the chromatogram having peaks corresponding to said substances A, C, D and E excluding the substance B is obtained, as shown in FIG. 30(A). On the contrary, according to the present invention, merely the chromatogram similar to that obtained by the conventional methods is obtained by the ultraviolet ray detector 37 of the liquid chromatograph 31 but the chromatogram obtained by the infrared ray detector 57 of the micro spectrometric analyzer 41 exhibits 5 peaks corresponding to 5 substances A to E, respectively. In short, according to the present invention, an existence of organic compounds, of which detection has been difficult by the conventional methods, can be detected and a substance can be estimated from retention times in the chromatogram of the liquid chromatograph 31.

In addition, some supplementary descriptions are added to the chromatogram shown in FIG. 30. Said retention times of the column are determined by the solute, the column and separating conditions, and, the ultraviolet ray detector 37 and the infrared ray detector 57 exhibit the same one retention times under the same one conditions. However, since they do not always coincide with each other in correlation between an ultraviolet ray sensitivity and an infrared ray sensitivity, the substance A is increased in absorbing sensitivity in the infrared ray detector 57 according to circumstances.

Figure 31:
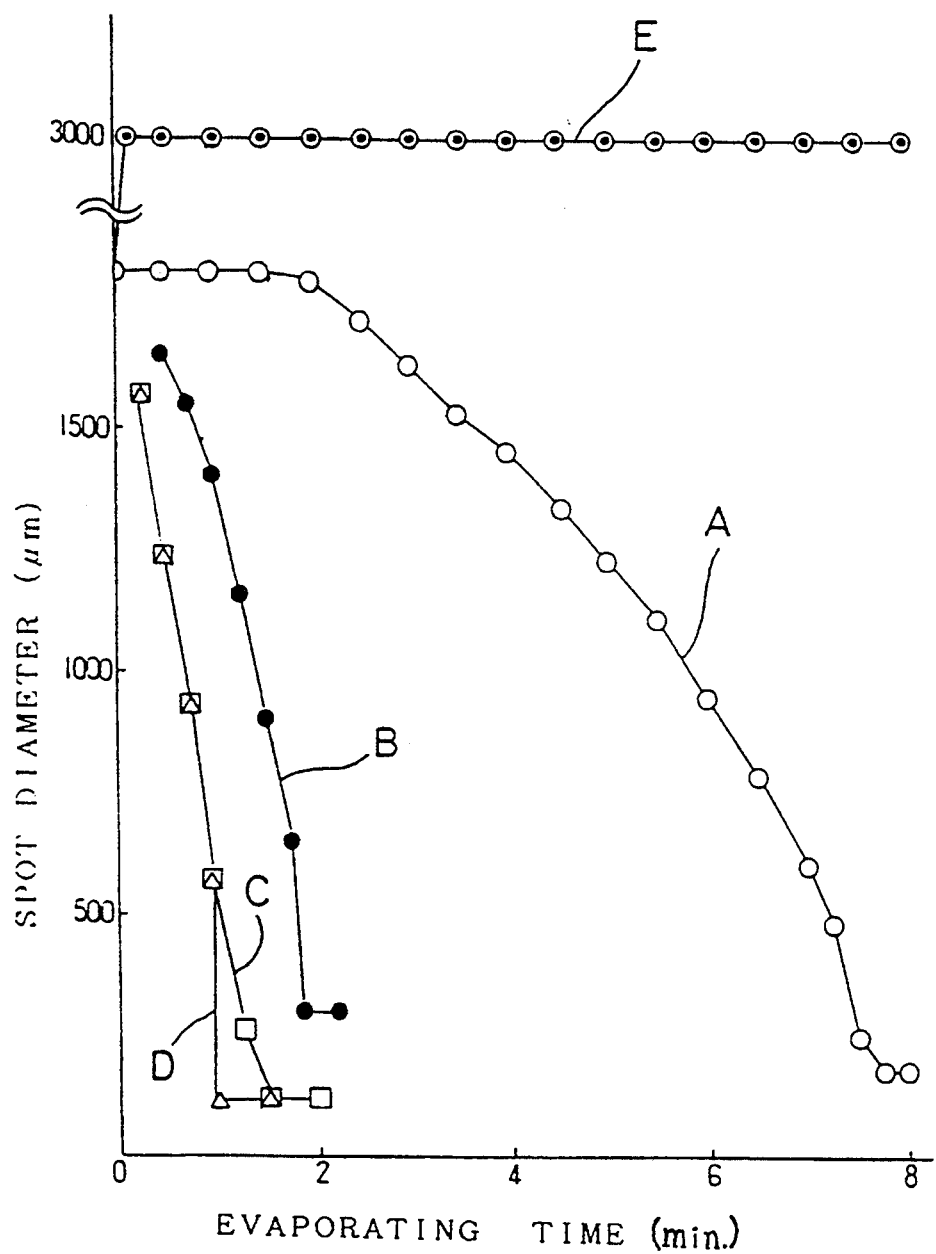
FIG. 31 is a diagram showing the change of spot diameter with the lapse of evaporating time when solutions of Triton in various kinds of solvent are deposited drop by drop on a thin film made of water-repellent fluoride resins.

In the above described preferred embodiment, the following effects are achieve. That is to say, since the solution L is deposited drop by drop on the thin film 48 made of the water-repellent fluoride resins by means of the dropping device 40 to evaporate the solvent, the high-speed measurement can be achieve. FIG. 31 shows a change of spot diameter with the lapse of evaporating time when the solution of Triton in various kinds of solvent was deposited drop by drop on the thin film 48 made of the fluoride resins. A curve A, B, C and D shows the solution L of Triton in water having normal temperature, water of 60° C., methanol having normal temperature and acetonitrile having normal temperature, respectively, at a concentration of 0.1 μg/ml. In addition, a curve E shows the comparative case where the solution L of Triton in water having normal temperature at the above described concentration was deposited drop by drop on a stainless steel plate.

It is found from the above described FIG. 31 that when for example water is used as the solvent, 1 μl of water can be evaporated for about 7 minutes at normal temperature and about 2 minutes at 60° C., and, similarly, methanol or acetonitrile can be evaporated for about 2 minutes.

As above described, according to the present invention, the solvent is removed from the solution L, so that the infrared absorption spectrum of the substance can be directly measured at every wavelength band within the infrared range. And, since the fluoride resins hardly have a spectrum and have the water-repellency, the spectrum of the substance is not influenced by the thin film 48 made of the fluoride resins even though the thin film 48 made of the fluoride resins is for example 1 μm or less thick. Rather, an absorption by fluorine is reduced and thus a detecting sensitivity is improved. However, if the thin film 48 is reduced in thickness, a control of evaporation and coherence is influenced by pinholes formed in addition to the desired pinholes during the formation of thin film according to circumstances.

And, as the solvent is evaporatedly removed, the solute is concentrated with the pinholes 49 as centers, so that a density of the samples S existing on the surface, upon which infrared rays are incident, is increased and thus the absorbing sensitivity is improved. Table 1 shows a coherent effect of the solution L or Triton, which is liquid at normal temperature, and 1,52O-dihydroxynaphthalene, which is solid at normal temperature, in 1 μl of methanol, acetonitrile and water, respectively, at a concentration of 100 μg/ml when the solution L was deposited drop by drop on a substrate made of a stainless steel (SUS), CaF$_2$ and PFE (fluoride resin), respectively, in an atmosphere of nitrogen gas of 25° C. In addition, Table 1, * represents "insoluble".

TABLE 1

| | Solute Diameter (μM) | | | | | |
|---|---|---|---|---|---|---|
| | Triton X-100 | | | 1,5-dihydroxynaphthalene | | |
| | Solvent | | | | | |
| | Meth. | Aceto. | H$_2$O | Meth. | Aceto. | H$_2$O |
| Substrate | | | | | | |
| SUS | 12000 | 4800 | 3000 | 12000 | 5200 | * |
| CAF$_2$ | 2200 | 2200 | 2200 | 2400 | 800 | * |
| PFP | 95 | 90 | 180 | 330 | 100 | * |

Figure 32:
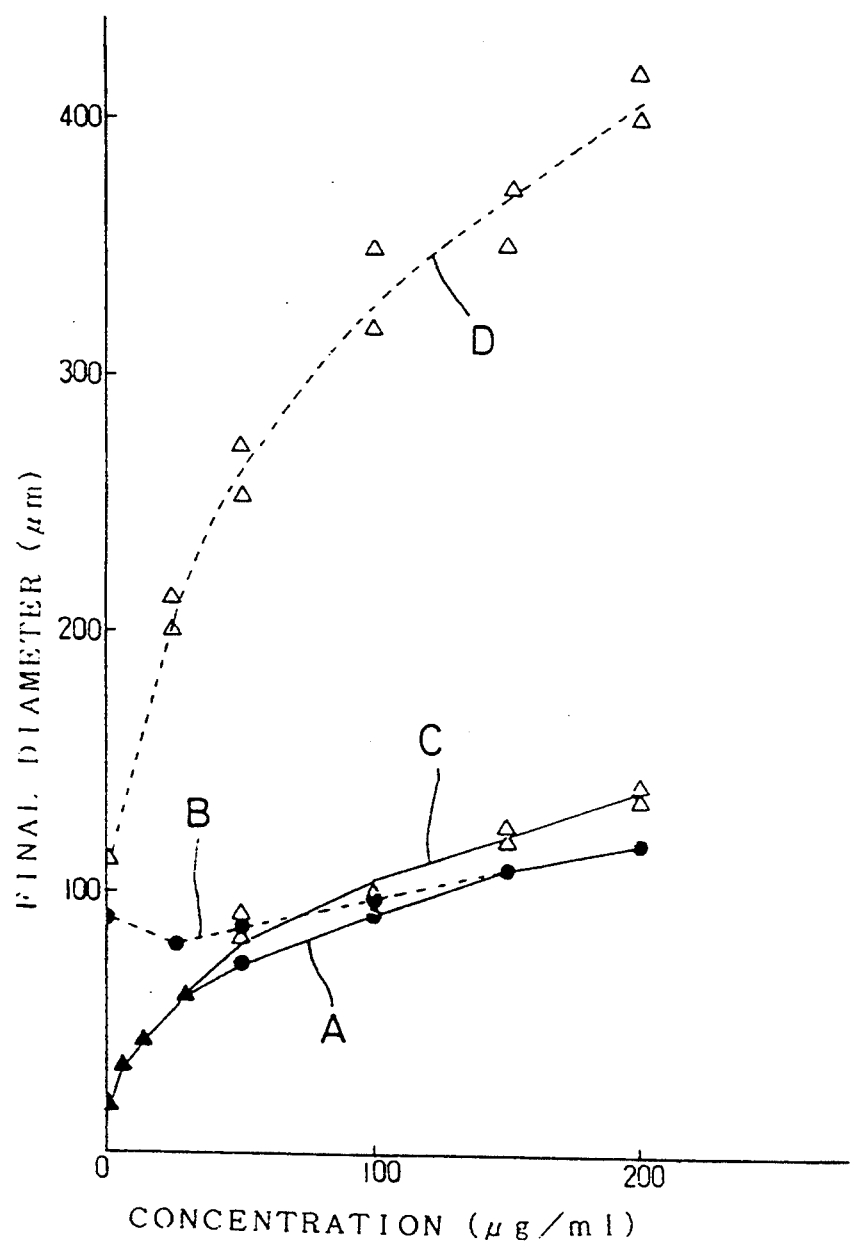
FIG. 32 is a diagram showing the relation between the concentration and final diameter of residues in solutions of Triton and 1, 5-dihydroxynaphthalene, respectively, in acetonitrile and methanol, respectively.

In addition, FIG. 32 shows a relation between a concentration and a final diameter of residues in the solution L of Triton and 1,5-dihydroxynaphthalene, respectively, in acetonitrile and methanol, respectively. In FIG. 32, a curve A shows the solution L of Triton in acetonitrile, a curve B the solution L of Triton in methanol, a curve C the solution L of 1,5-dihydroxynaphthalene in acetonitrile and a curve D the solution L of 1,5-dihydroxynaphthalene in methanol, respectively. It is found from FIG. 32 that said final diameter of residues amounts to about 400 μm at said concentration of 200 μg/ml in the solution L of 1.5-dihydroxynaphthalene in methanol.

Figure 33:
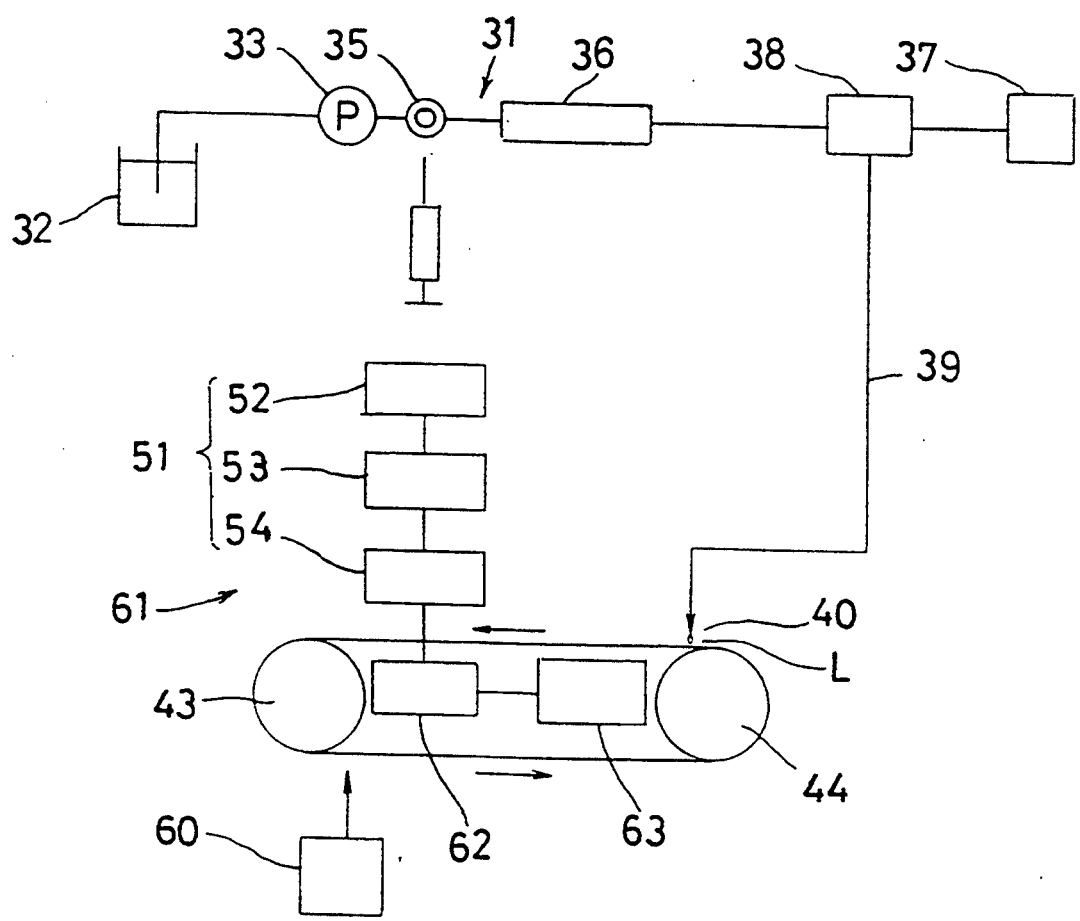
FIG. 33 is a diagram roughly showing the construction of an apparatus for detecting organic compounds according to another preferred embodiment of the present invention.

FIG. 33 roughly shows a construction of an apparatus for detecting organic compounds according to another preferred embodiment. A micro spectrometric analyzer 61 in this preferred embodiment is constructed so as to measure by the transmission of infrared rays. That is to say, that sampling plate 47 is formed of materials transmissive to infrared rays, such as crystals or films made of alkali halide materials, for example NaCl or CaF$_2$, and the conveying belt 45 if formed not so as to hinder the transmission of infrared rays. And, an infrared ray detector 62 is provided at a position where the infrared rays, which have transmitted through the sample S and the sampling plate 47, are to be received. In addition, reference numeral 63 designates an amplifier. An operation in this preferred embodiment, so that its detailed description is omitted.

The present invention is not limited by the above described preferred embodiments and a differential refractometer may be used in place of the ultraviolet ray detector 37 in FIGS. 26 and 33. In addition, a spectrometric element may be used in place of the filter 53. And, although the pinholes 49 are formed as the condensing nuclei of the solution L deposited drop by drop on the thin film 48 made of the fluoride resins in the above described preferred embodiment, the thin film 48 made of the fluoride resins may be irradiated with laser beams or ultraviolet rays at appointed places thereof to reduced very small zones in surface tension.

Furthermore, in the case where the sample S is irradiated with infrared rays in the micro spectrometric analyzers 41, 61, said infrared rays all over the bands may be irradiated to investigate the absorbing degree at the specified wavelength band, or, the infrared rays of the specified wavelength band may be irradiated to investigate a change of intensity thereof. For example, said change of absorbing intensity at the specified wavelength (for example an absorption band due to an expansion and contraction of C—H of 3,100 to 2,900 cm$^{-1}$ and an absorption band due to a variable angle oscillation or an inverted symmetrical variable angle oscillation of C—H of 1,300 to 1,500 cm$^{-1}$ exhibit a remarkably increased absorbing intensity) is measured, so that the analysis can be achieved in high sensitivity.

As above described, according to the method of detecting organic compounds according to the present invention, an existence and concentrations of organic compounds, which have not been able to detect by the conventional methods, can be detected. That is to say, a detection limit in the conventional methods was $1 \times 10^{-6}$ g but that in the method according to the present invention was improved to $10 \times 10^{-12}$ g.

Besides, the apparatus according to the present invention, the exclusive FTIR is not used differently from the conventional methods, so that the apparatus is simplified in construction and inexpensive.

By the way, in the preferred embodiments shown in FIGS. 26 and 33, the liquid eluted from the column 36 was divided into the ultraviolet ray detector 37 and the micro spectrometric analyzer 41 at the suitable shunting ratio in the device for making a liquid branch 38.

Figure 35:
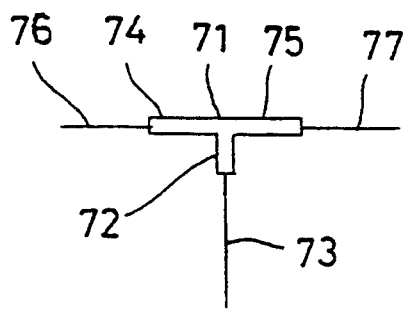
FIG. 35 is a diagram showing one example of a branching T-type joint to which the above described method of making a liquid branch is applied.

FIG. 35 is a diagram showing one example of the device for making a liquid branch 38. Referring to FIG. 35, reference numeral 71 designates a T-type branching joint provided with a passage 73 (connected with a passage connected with the column of the liquid chromatograph on the upstream side thereof), through which a liquid to be shunted flows upward from below, connected with a connecting portion 72 extending downward therefrom and a shunting passage 76, 77 connected with a right and left connecting portion 74,75, respectively, meeting at right angeles with said connection portion 72. In this preferred embodiment, a flexible tube made of fluoride resins (Teflon made by DuPont) is used as said shunting passages 76, 77.

Figure 34:
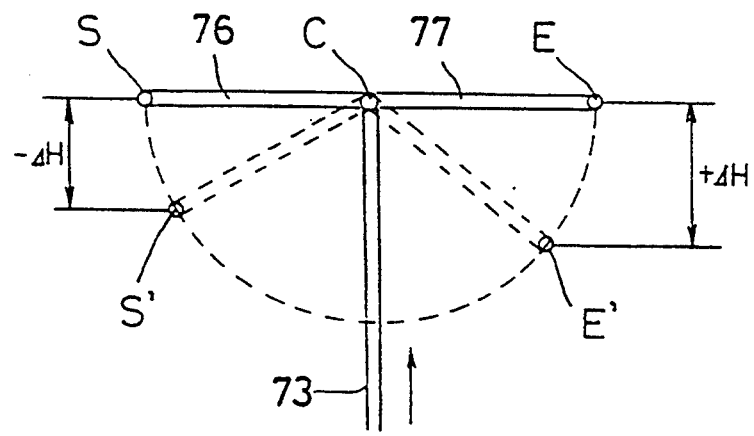
FIG. 34 is a diagram showing a method of making a liquid flowing through one passage branch into two passages at a junction.

In order to more concretely describe it, said construction shown in FIG. 35 is illustrated in FIG. 34. That is to say, referring to FIG. 34, C designates a junction and S, E designates said outlet end of the tube 76, 77, respectively. And, said height of the outlet end S, E of each tube 76, 77 is relatively changed by moving said outlet end E (or S) of the tube 77 (or 76) downward along a semicircle shown by an imaginary line under the condition that the outlet end S (or E) of the other tube 76 (or 77) is held at the same height as said junction C, in short the tube 76 (or 77) is held horizontally.

Now, provided that a difference between the outlet end E and the junction C as the standard when the outlet end E was lowered to a position shown by a mark E' in height is+ΔH, a difference between the outlet end S and the junction C as the standard when the outlet end S was lowered to a position shown by a mark S' in height being—ΔH, both the tubes 76, 77 having a nominal outside diameter of 1.5 mm, the tube 76 having a nominal inside diameter of 0.25 mm, the tube 77 having a nominal inside diameter of 0.5 mm, and their lengths, in short a distance between C and S and a distance between C and E, being for example 300 mm equal to each other.

The flow rate of liquid flowing on the side of the outlet end S and side of the outlet end E, respectively, when a position of the outlet end S or the outlet end E of the tube 76 or 77 was changed (lowered) in the above described manner is shown in the following Tables 2 and 3.

TABLE 2

| Difference ΔH (mm) S = 0 0 − E' = + ΔH | Flow rate of liquid on the side of S (ml/min) | Flow rate of liquid on the side of E (ml/min) | Shunting ratio (S/E) |
| --- | --- | --- | --- |
| 0 | 3.55 | 18.75 | 0.178 |
| 20 | 3.0 | 18.9 | 0.153 |
| 40 | 2.55 | 18.7 | 0.137 |
| 60 | 2.2 | 18.9 | 0.116 |
| 80 | 1.55 | 17.6 | 0.088 |
| 100 | 1.25 | 18.0 | 0.069 |
| 120 | 1.09 | 19.1 | 0.057 |
| 140 | 0.89 | 20.2 | 0.044 |

TABLE 3

| Difference ΔH (mm) S = 0 0 − S′ = − ΔH | Flow rate of liquid on the side of S (ml/min) | Flow rate of liquid on the side of E (ml/min) | Shunting ratio (S/E) |
| --- | --- | --- | --- |
| 0 | 3.55 | 18.75 | 0.178 |
| 20 | 3.5 | 16.6 | 0.210 |
| 40 | 4.15 | 16.9 | 0.245 |
| 60 | 4.35 | 16.4 | 0.265 |
| 80 | 4.5 | 15.3 | 0.294 |
| 100 | 5.0 | 15.8 | 0.316 |
| 120 | 5.15 | 15.4 | 0.334 |
| 140 | 5.45 | 15.15 | 0.359 |

That is to say, Table 2 shows the change of the flow rate of liquid on the side of the outlet end S and the side of the outlet end E, respectively, when the outlet end S is held at the same height as the junction C and the outlet end E was lowered by 20 mm in FIG. 34, while Table 3 shows the change of the flow rate of liquid on the side of the outlet end S and the side of the outlet end E, respectively, when the outlet E is held at the same height as the junction C and the outlet end S was lowered by 20 mm in FIG. 34. In addition, the flow rate of liquid to the junction C at this time was integrated for 20 minutes at 1 ml/min.

And, in Tables 2 and 3, the shunting ratio represents a ratio of the flow rate of liquid flowing on the side of S to that flowing on the side of E. When ΔH=0, the tubes 76, 77 are held at the heights equal to each other, so that no difference is produced between the outlet end S and the outlet end E in height and thus the shunting ratio S/E amounts to a value corresponding to a ratio of a sectional area of the tube 76 to that of the tube 77 but it can be expressed by the following function (1) by the difference ΔH between the outlet end S and the outlet end E in height (until the vicinity of ΔH=100).

That is to say, $S/E - K \cdot (\Delta H)$ = sectional area of the outlet end S/sectional area of the outlet end E—(1) wherein K represents a constant determined according to the liquid.

Figure 36:
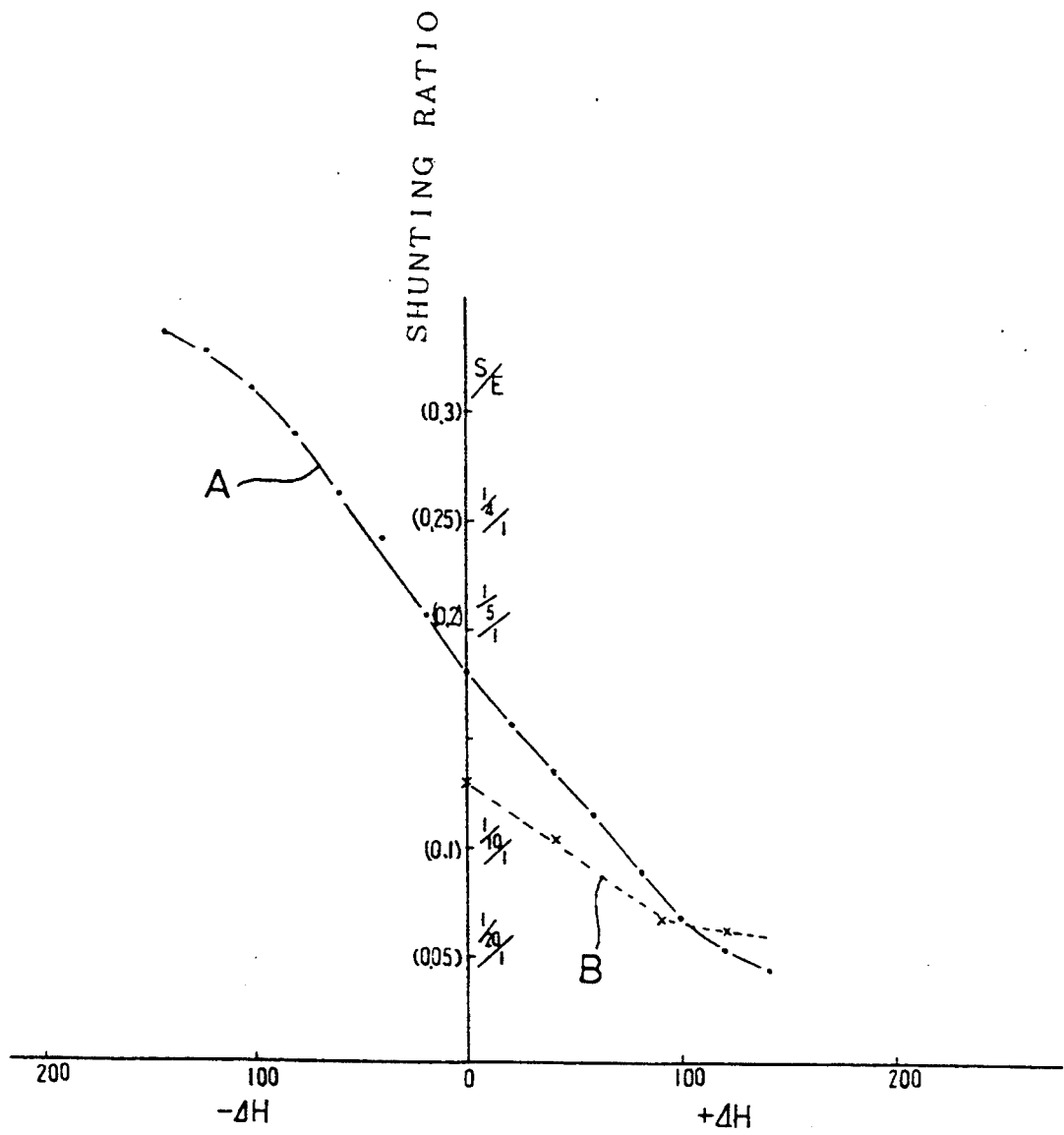
FIG. 36 is a graph showing the change of shunting ratio when a liquid is made to branch into two pieces of tube having inside diameters different from each other.

FIG. 36 is a graph showing a change of shunting ration S/E. Referring to FIG. 36, a curve A shown by a full line shows the change of shunting ratio S/E when an eluting liquid (comprising normal hexane and methanol) used in the liquid chromatography was shunted while a curve B shown by a dotted line shows the change of shunting ratio S/E when water was shunted.

It is found from FIG. 36 that is case of said eluting liquid comprising normal hexane and methanol, the shunting ratio S/E can be continuously all over about one figure from 0.044 to 0.359 with 0.178 as a center. In addition, in case of water, the effect was reduced as compared with said case of the eluting liquid.

Figure 37:
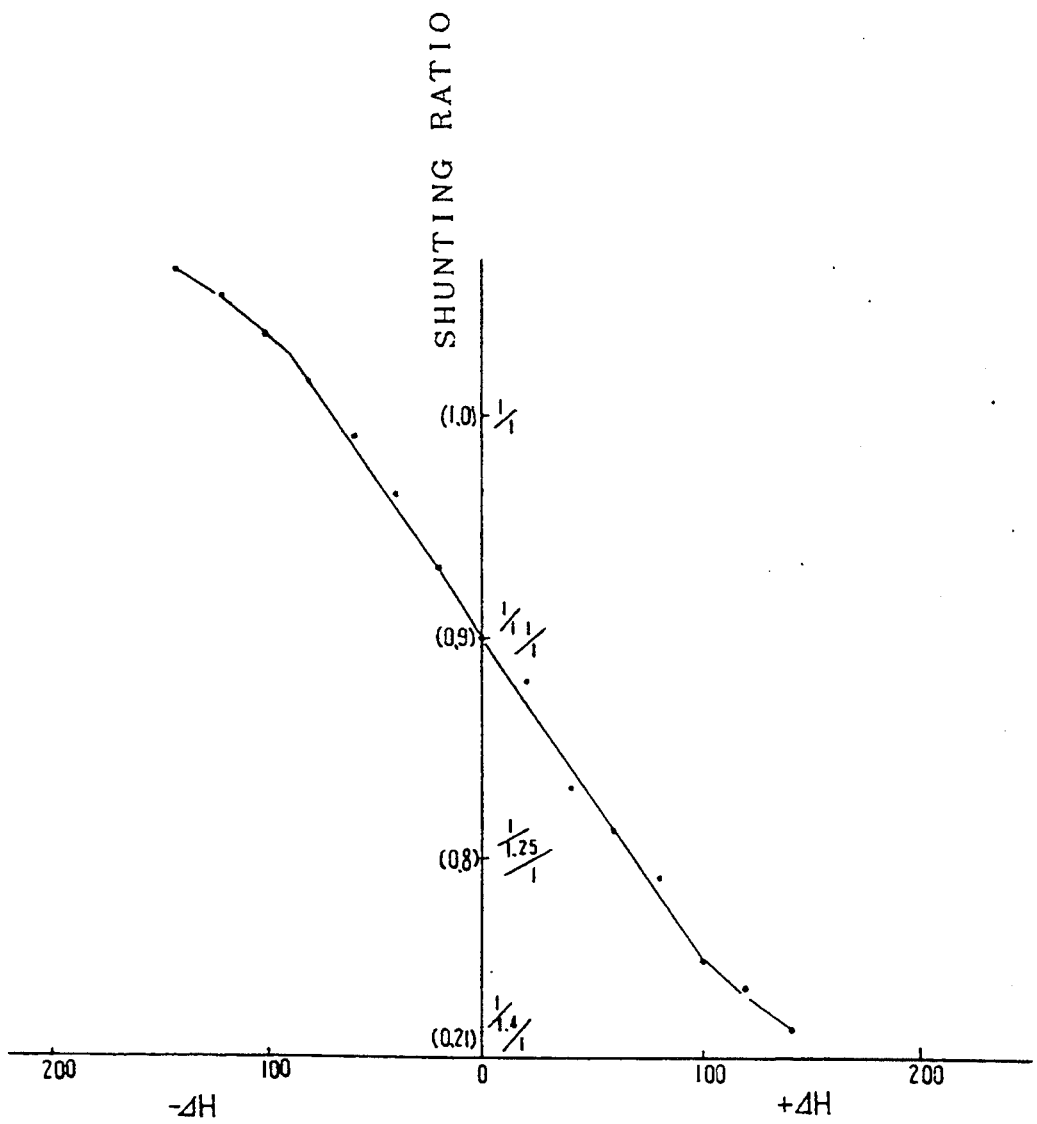
FIG. 37 is a graph showing the change of shunting ratio when a liquid is made to branch into two pieces of tube having inside diameters equal to each other.
Figure 38:
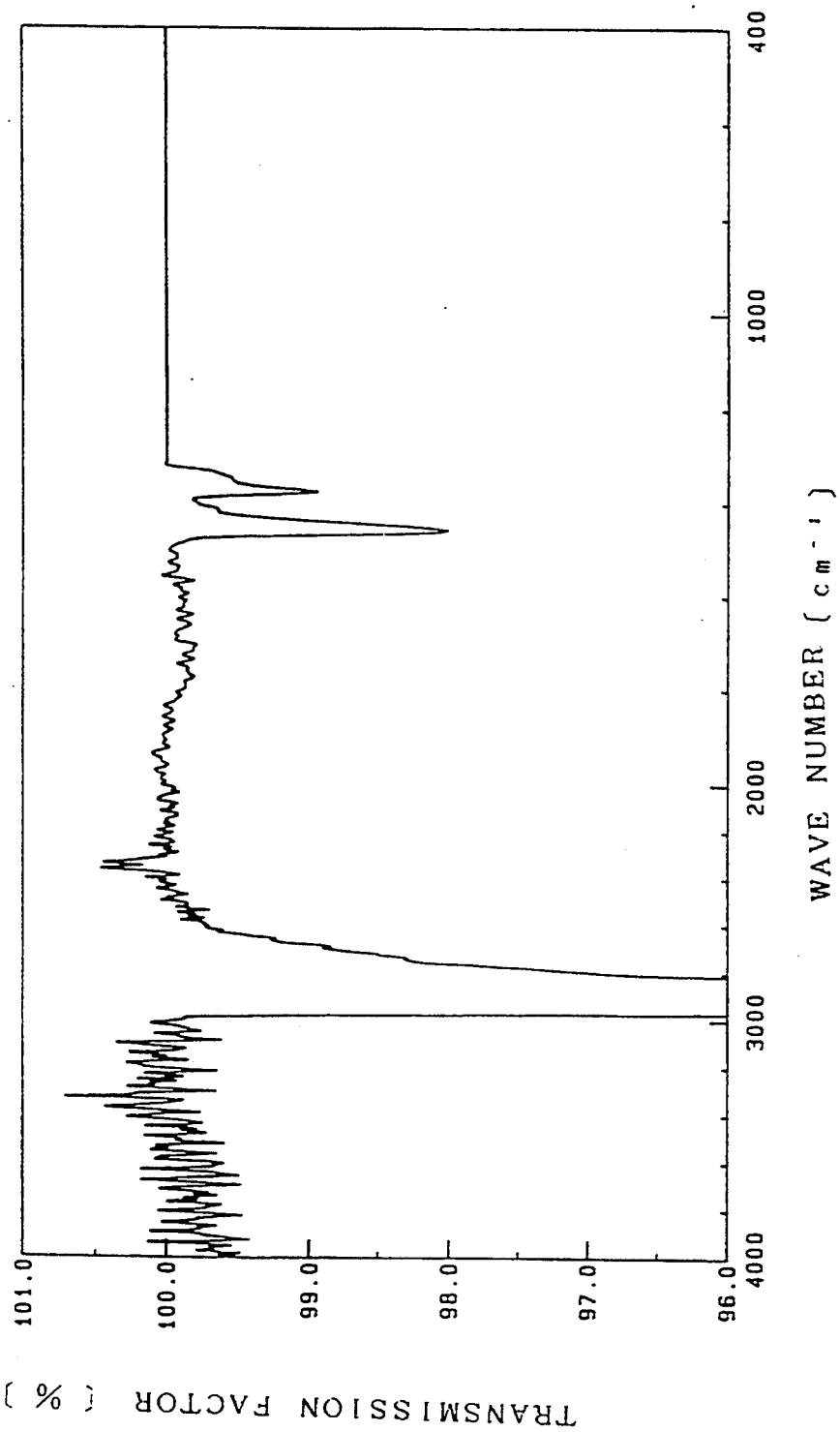
FIG. 38 is a diagram showing transmission characteristics of infrared rays using a conventional method of making a liquid branch.
Figure 39:
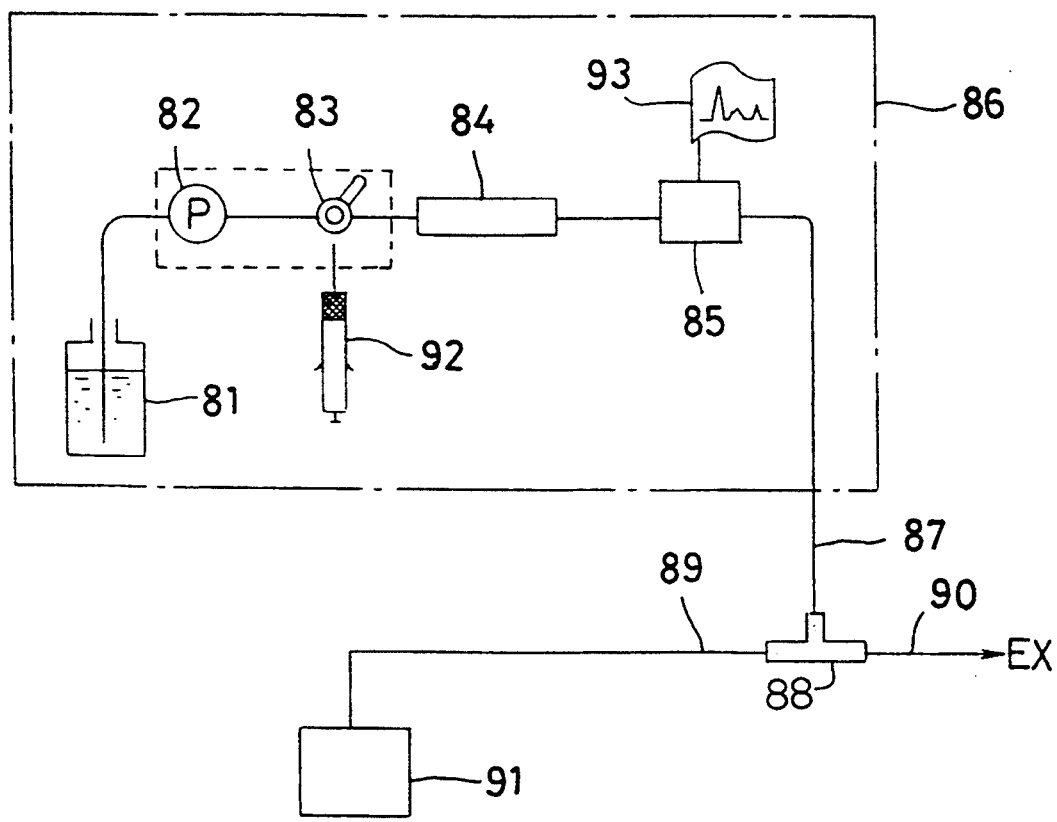
FIG. 39 is a diagram showing a conventional method of making a liquid branch.

FIG. 37 is a graph showing the change of shunting ratio S/E when the eluting liquid was shunted in the same manner as above described by the use of two pieces of tube (equal to each other in length) having the same inside diameter.

As above described, according to the above described preferred embodiment, that ratio of the flow rate of liquid flowing through the tube 76 to that flowing through the tube 77 can be optionally and continuously changed by merely relatively changing the heights of the respective outlet ends of the tubes 76, 77. And, no flow rate-controlling instrument, such as needle value, is used, so that the eluting liquid is not made turbulent in current at all and thus no expansion is produced in the chromatogram and no difficulty in keeping the resolution power is observed.

Although the above described preferred embodiment has such the construction that the liquid to be divided flows from below toward the junction C, the direction of the liquid flowing toward the junction C is optionally selected. And, it goes without saying that the branching passages 76, 77 may be formed of a pipe made of materials other than the above described Teflon. In addition, the method according to the present invention can be applied also to the case where the eluting liquid used in the liquid used in the liquid chromatograph is introduced into a mass analyzer.

As above described, according to the present invention, in the case where the liquid flowing through one passage is shunted into two passages at the junction, the ratio of the flow rate of liquid flowing one passage to that flowing the other passage can be optionally and continuously changed by merely relatively changing the heights of the respective outlet ends of two branched passages, in particular a small flow rate of liquid, such as the eluting liquid of the liquid chromatograph, can be divided sampled at an optional ratio.

We claim:

1. A micro spectrometric analytical method comprising:
    depositing microliter quantities of a solution of a solute in a solvent drop by drop on a water-repellent thin film applied to an infrared ray-reflecting material,
    evaporating said solvent to provide a sample,
    irradiating said sample with infrared radiation, and
    measuring the infrared spectrum reflected from said infrared ray-reflecting material through said sample.

2. The method of claim 1 wherein said water-repellent thin film comprises a thin film of fluoride resins.

3. The method of claim 1 wherein said water-repellent thin film contains a multiplicity of depressions into which said solution is deposited and which serve as condensing nuclei for said solution.

4. The method of claim 1 wherein said water-repellent thin film contains a multiplicity of pinholes into which said solution is deposited and which serve as condensing nuclei for said solution.

5. A micro spectrometic analytical method comprising:
    depositing microliter quantities of a solution of a solute in a solvent drop by drop on a water-repellent thin film applied to an infrared ray-transmitting material,
    evaporating said solvent to provide a sample,
    irradiating said sample with infrared radiation, and
    measuring the infrared spectrum transmitted through said sample and said infrared ray-transmitting material.

6. The method of claim 5 wherein said water-repellent thin film comprises a thin film of fluoride resins.

7. The method of claim 5 wherein said water-repellent thin film contains a multiplicity of depressions into which said solution is deposited and which serve as condensing nuclei for said solution.

8. The method of claim 5 wherein said water-repellent thin film contains a multiplicity of pinholes into which said solution is deposited and which serve as condensing nuclei for said solution.

9. A micro spectrometric analytical method comprising:
depositing microliter quantities of a solution of a solute in a solvent drop by drop on a water-repellent base,
evaporating said solvent to provide a sample, transferring said sample to an infrared ray-reflecting material,
irradiating said sample with infrared radiation, and
measuring the infrared spectrum reflected from said infrared ray-reflecting material through said sample.

10. The method of claim 9 wherein said water-repellent base comprises a thin film of fluoride resins.

11. The method of claim 9 wherein said water-repellent base contains a multiplicity of depressions into which said solution is deposited and which serve as condensing nuclei for said solution.

12. The method of claim 9 wherein said water-repellent base contains a multiplicity of pinholes into which said solution is deposited and which serve as condensing nuclei for said solution.

13. A micro spectrometric analytical method comprising:
depositing microliter quantities of a solution of a solute in a solvent drop by drop on a water-repellent base,
evaporating said solvent to provide a sample,
transferring said sample to an infrared ray transmitting material,
irradiating said sample with infrared radiation, and
measuring the infrared spectrum transmitted through said sample and said infrared ray-transmitting material.

14. The method of claim 13 wherein said water-repellent base comprises a thin film of fluoride resins.

15. The method of claim 13 wherein said water-repellent base contains a multiplicity of depressions into which said solution is deposited and which serve as condensing nuclei for said solution.

16. The method of claim 13 wherein said water-repellent base contains a multiplicity of pinholes into which said solution is deposited and which serve as condensing nuclei for said solution.

17. A sampling plate comprising a water-repellent thin film applied to an infrared ray-reflecting material.

18. A sampling plate of claim 17 wherein said water-repellent thin film comprises a thin film of fluoride resins.

19. A sampling plate of claim 17 wherein said water-repellent thin film contains a multiplicity of depressions which may serve as condensing nuclei for a solution being evaporated.

20. A sampling plate of claim 17 wherein said water-repellent thin film contains a multiplicity of pinholes which may serve as condensing nuclei for a solution being evaporated.

21. A sampling plate comprising a water-repellent thin film applied to an infrared ray-transmitting material.

22. The sampling plate of claim 21 wherein said water-repellent thin film comprises a thin film of fluoride resins.

23. A sampling plate of claim 21 wherein said water-repellent thin film contains a multiplicity of depressions which may serve as condensing nuclei for a solution being evaporated.

24. A sampling plate of claim 21 wherein said water-repellent thin film contains a multiplicity of pinholes which may serve as condensing nuclei for a solution being evaporated.

25. A method of detecting organic compounds, in which a liquid eluted from a column of a liquid chromatograph is deposited drop by drop on a thin film of water-repellent fluoride resins applied to an infrared ray-reflecting material and a sample of organic compounds coherently concentrated on said think film is irradiated with infrared rays to detect reflected infrared rays and measure the absorbing degree of said reflected infrared rays, thereby detecting the existence and concentration of said organic compounds.

26. A method of detecting organic compounds, in which a liquid eluted from a column of a liquid chromatograph is deposited drop by drop on a thin film of water-repellent fluoride resins applied to an infrared ray-transmitting material and a sample of organic compounds coherently concentrated on said thin film is irradiated with infrared rays to detect transmitted infrared rays and measure the absorbing degree of said transmitted infrared rays, thereby detecting the existence and concentration of said organic compounds.

27. An apparatus of detecting organic compounds comprising a column of a liquid chromatograph, a device for dropping a liquid from said column, a sampling plate provided with a thin film of water-repellent fluoride resins formed on a surface thereof, a sampler for conveying said sampling plate at an appointed speed in an appointed direction, an infrared ray-irradiating device for irradiating a sample coherently concentrated on said thin film with infrared rays, and an infrared ray-detecting portion for detecting infrared rays reflected from said sampling plate when said sample is irradiated with said infrared rays.

28. An apparatus of detecting organic compounds comprising a column of a liquid chromatograph, a device for dropping a liquid from said column, a sampling plate provided with a thin film of water-repellent fluoride resins formed on a surface thereof, a sampler for conveying said sampling plate at an appointed speed in an appointed direction, an infrared ray-irradiating device for irradiating a sample coherently concentrated on said thin film with infrared rays, and an infrared ray-detecting portion for detecting infrared rays, which have transmitted through said sample and said sampling plate, when said sample is irradiated with said infrared rays.

* * * * *

UNITED STATES PATENT AND TRADEMARK OFFICE
CERTIFICATE OF CORRECTION

PATENT NO. : 5,334,837
DATED : August 2, 1994
INVENTOR(S) : Ikeda et al.

It is certified that error appears in the above-indentified patent and that said Letters Patent is hereby corrected as shown below:

Claim 25 (column 26, line 20), delete "think" and substitute therefor ---thin---.

Signed and Sealed this

Thirty-first Day of January, 1995

Attest:

BRUCE LEHMAN

*Attesting Officer*　　　　*Commissioner of Patents and Trademarks*